(12) United States Patent
Bastian et al.

(10) Patent No.: US 10,323,019 B2
(45) Date of Patent: Jun. 18, 2019

(54) PYRAZOLYLAMINOBENZIMIDAZOLE DERIVATIVES AS JAK INHIBITORS

(71) Applicant: Eli Lilly and Company, Indianapolis, IN (US)

(72) Inventors: Jolie Anne Bastian, Indianapolis, IN (US); Joshua Ryan Clayton, Fishers, IN (US); David Andrew Coates, New Palestine, IN (US); Daniel Jon Sall, Greenwood, IN (US); Timothy Andrew Woods, Edinburgh, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/775,990

(22) PCT Filed: Jul. 10, 2017

(86) PCT No.: PCT/US2017/041388
§ 371 (c)(1),
(2) Date: May 15, 2018

(87) PCT Pub. No.: WO2018/013486
PCT Pub. Date: Jan. 18, 2018

(65) Prior Publication Data
US 2018/0325873 A1    Nov. 15, 2018

Related U.S. Application Data

(60) Provisional application No. 62/362,208, filed on Jul. 14, 2016.

(51) Int. Cl.
| C07D 401/14 | (2006.01) |
| C07D 403/14 | (2006.01) |
| A61K 31/4184 | (2006.01) |
| A61K 31/4439 | (2006.01) |
| A61P 37/00 | (2006.01) |
| A61P 19/02 | (2006.01) |
| A61P 1/00 | (2006.01) |
| C07D 403/12 | (2006.01) |

(52) U.S. Cl.
CPC ........ *C07D 401/14* (2013.01); *A61K 31/4184* (2013.01); *A61K 31/4439* (2013.01); *A61P 1/00* (2018.01); *A61P 19/02* (2018.01); *A61P 37/00* (2018.01); *C07D 403/12* (2013.01); *C07D 403/14* (2013.01)

(58) Field of Classification Search
CPC ........................... C07D 401/14; C07D 403/14
See application file for complete search history.

(56) References Cited

U.S. PATENT DOCUMENTS

| 9,440,929 | B2 | 9/2016 | Menet et al. | |
| 9,556,153 | B1* | 1/2017 | Clayton | A61K 31/4184 |
| 2011/0201593 | A1* | 8/2011 | Babu | C07D 471/14 |
| | | | | 514/210.18 |
| 2014/0228348 | A1* | 8/2014 | Brubaker | C07D 403/12 |
| | | | | 514/210.18 |
| 2015/0203455 | A1 | 7/2015 | Menet | |

FOREIGN PATENT DOCUMENTS

WO    2017/023672 A1    2/2017

* cited by examiner

*Primary Examiner* — Matthew P Coughlin
(74) *Attorney, Agent, or Firm* — Nelsen L Lentz; James B Myers

(57) ABSTRACT

The present invention provides compounds of the formula below (I'): where R, and R1-R3 are as described herein, methods of treating patients for certain types of autoimmune diseases and cancer, and processes for preparing the compounds.

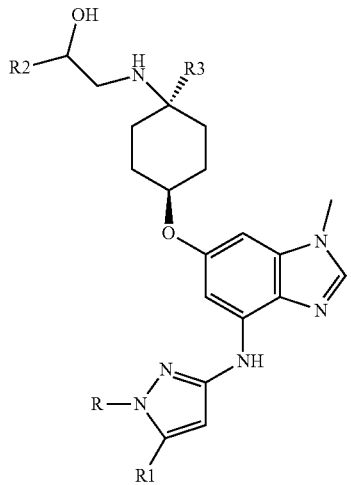

18 Claims, No Drawings

PYRAZOLYLAMINOBENZIMIDAZOLE DERIVATIVES AS JAK INHIBITORS

The present invention relates to benzimidazole compounds and their pharmaceutically acceptable salts, that inhibit Janus kinase 1 (JAK1), pharmaceutical compositions comprising the compounds, methods of using the compounds to treat certain types of autoimmune diseases and cancer, and processes for preparing the compounds.

The family of Janus kinases (JAK1, JAK2, JAK3 and TYK2) are intracellular protein tyrosine kinases with essential roles in immune function, inflammation, and hematopoiesis through the Janus kinase-signal transducer and activator of transcription (the JAK-STAT) pathway. In response to extracellular polypeptides such as type I and type II cytokines, the Janus kinases regulate the tyrosine phosphorylation of various effectors and initiate activation of downstream signaling pathways inducing different physiological responses. Specifically the JAK1 isoform plays a key role in types I and II interferon signaling and elicits signals from the interleukin-2 (IL-2), interleukin-4 (IL-4), glycoprotein 130 (gp130) and class II receptor families. As such, small molecule inhibition of JAK1 may intervene in the signaling pathways involved in oncology, inflammation and autoimmune diseases. Ghoreschi K et al. Immunological Review 2009, 228, 273-287 and Zak M. et al. Med Chem. 2013, 56, 4764-4785.

Despite the recent successes of JAK inhibitor agents, there is still a need to discover and develop inhibitors, which selectively target a single JAK isoform. This can mitigate the risk of off target affects.

Janus kinase inhibitor compounds are known in the literature. For example, US 2015/0203455 discloses certain benzimidazole compounds that are JAK inhibitors and which are touted as being useful to treat autoimmune diseases, inflammatory diseases and proliferative diseases inter alia.

There remains a need to provide alternative JAK1 inhibitors for treatment of autoimmune diseases particularly for immunological diseases, such as arthritis, rheumatoid arthritis, and diabetic nephropathy. In addition, there remains a need to provide selective JAK1 inhibitors. The present invention provides certain inhibitors of JAK1, which can address one or more of these needs.

The present invention provides a compound of Formula 1, or a pharmaceutically acceptable salt thereof:

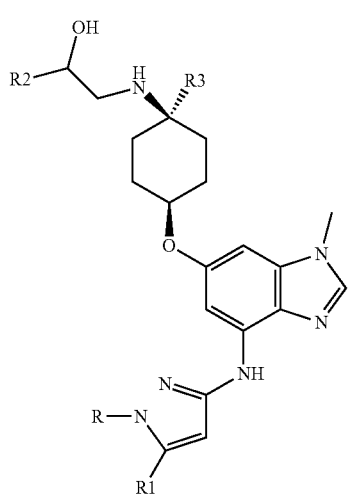

where R is selected from: H, —$C_{1-3}$ alkyl, —$CH_2CH(OH)CH_3$, or —$C_{2-3}$ alkyl-O—$CH_3$,

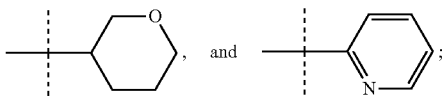

R1 is selected from: H, —$CH_3$ and —$OCH_3$; R2 is —$CHF_2$ or —$CF_3$; and R3 is H or —$CH_3$; provided that when R2 is —$CF_3$ and R3 is H, either R or R1 can be —$CH_3$ but not both. The bond illustrated as

indicates the point of attachment of the tetrahydropyran ring or pyridine ring to the rest of the molecule.

The present invention provides a compound of Formula 2, or a pharmaceutically acceptable salt there, which is,

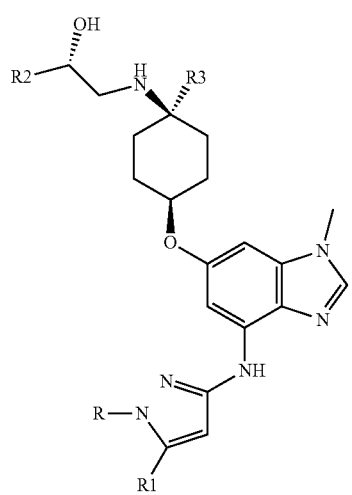

where R is selected from: H, —$C_{1-3}$ alkyl, —$CH_2CH(OH)CH_3$, or —$C_{2-3}$ alkyl-O—$CH_3$,

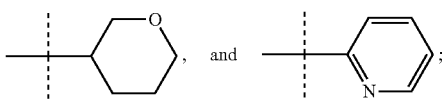

R1 is selected from: H, —$CH_3$ and —OCH; R2 is —$CHF_2$ or —$CF_3$; and R3 is H or —$CH_3$; provided that when R2 is —$CF_3$ and R3 is $CH_3$, either R or R1 can be —$CH_3$ but not both.

In one form, the present invention provides a compound according to Formula 1 or 2 where R is selected from: —$CH_3$, —$CH_2CH_3$, and

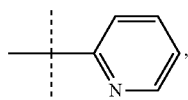

or a pharmaceutically acceptable salt thereof. In certain embodiments. R is —CH₃, or —CH₂CH₃. In other embodiments, R is

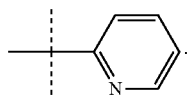

In another form the present invention provides a compound according to Formula 1 or 2 where R is

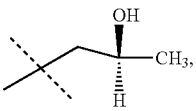

where the bond illustrated as

indicates the point of attachment to the rest of the molecule. In another form, the present invention provides a compound according to Formula 1 or 2 where R is

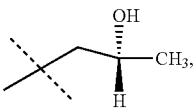

In another form, the present invention provides a compound according to Formula 1 or 2 where R1 is selected from: H, —CH₃, and —OCH₃. In certain embodiments R1 is H or —CH₃. In other embodiments, R1 is —OCH₃.

In another form, the present invention provides a compound according to Formula 1 or 2 where R2 is —CF₃. In certain embodiments of this form, R is —CH₃, or —CH₂CH₃ and R1 is —CH₃, or —OCH₃. In other embodiments of this form, R is

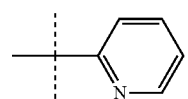

and R1 is H.

In another form, the present invention provides a compound according to Formula 1 or 2 wherein R3 is —CH₃. In certain embodiments R is H, R1 is H, and R2 is CH₃.

In one embodiment, the present invention provides a compound of Formula 3 which is

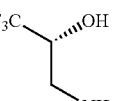

or a pharmaceutically acceptable salt thereof.

In another embodiment, the present invention provides a compound of Formula 4 which is

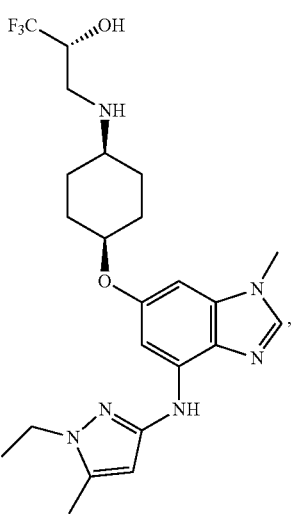

or a pharmaceutically acceptable salt thereof.

In yet another embodiment, the present invention provides a compound of Formula 5, which is

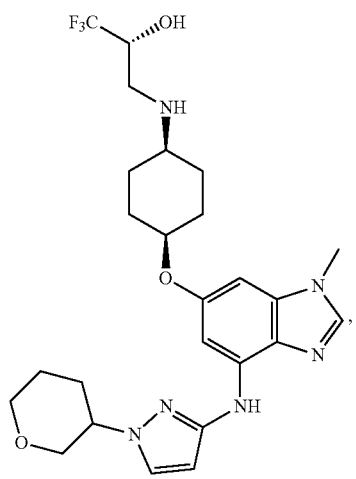

5 or a pharmaceutically acceptable salt thereof.

In another embodiment, the present invention provides a compound of Formula 5A, which is:

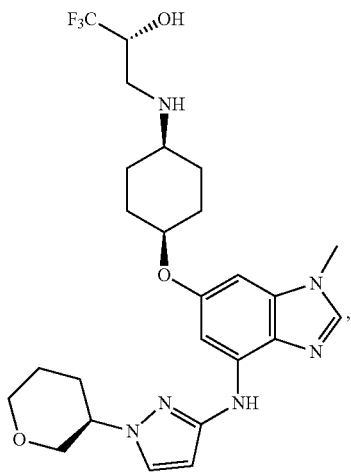

5A or a pharmaceutically acceptable salt thereof.

In another embodiment, the present invention provides a compound of Formula 5B, which is:

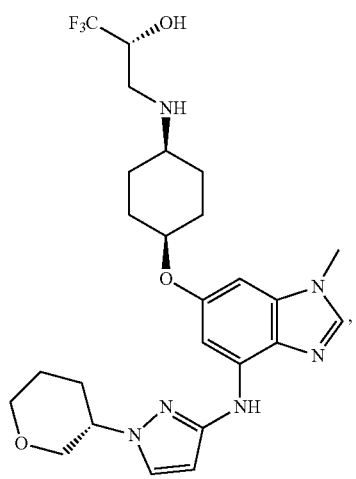

5B or a pharmaceutically acceptable salt thereof.

In yet another embodiment, the present invention provides a compound of Formula 6 which is

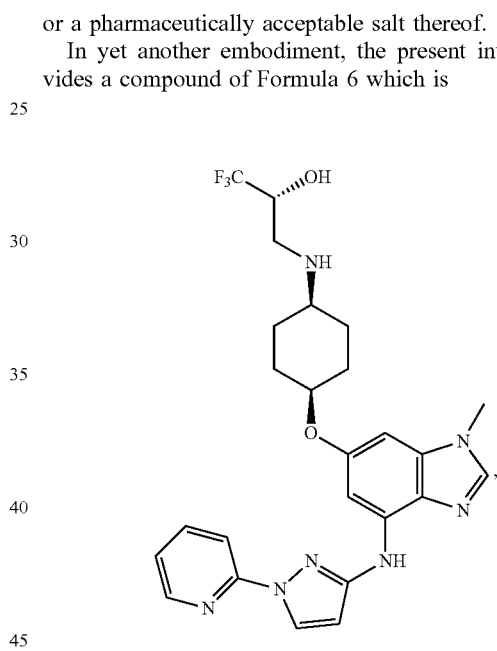

6 or a pharmaceutically acceptable salt thereof. In one embodiment the pharmaceutical composition comprises a compound of Formula 6 as a neutral compound as a free base or zwitterion. In one embodiment, the present invention provides the compound of Formula 6 as a citrate salt. In still yet another embodiment, the present invention provides a compound of Formula 6 as free base in crystalline form characterized by an X-ray powder diffraction pattern obtained from a CuKα source (λ=1.54056 Å), which comprises peaks at: 15.5, 18.1, 18.3, 20.5, and 22.9+/−0.2° in 2 theta, or 13.2, 15.5, 18.1, 18.3, 18.5, 20.5, 22.9, and 23.6, 23.7, +/−0.2° in 2 theta, or 13.2, 15.5, 18.1, 18.3, 18.5, 19.0, 20.5, 22.9, 23.6, 23.6, 23.7, 24.7, and 26.5+/−0.2° in 2 theta.

In still yet another embodiment, the present invention provides a compound of Formula 6 as (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)pro-pan-2-ol 2-hydroxypropane-1,2,3-tricarboxylate hydrate (1:1:1) in crystalline form characterized by an X-ray powder diffraction pattern obtained from a CuKα source (λ=1.54056 Å), which comprises peaks at: 18.6, 19.1, 21.0, and 22.4+/−

0.2° in 2 theta, or 7.4, 11.0, 18.6, 19.1, 21.0, 21.9, 22.4, and 26.2+/−0.2° in 2 theta or 7.4, 11.0, 12.7, 16.8, 18.6, 19.1, 21.0, 21.9, 22.4, and 26.2, +/−0.2° in 2 theta.

In another form, the present invention provides a composition comprising substantially pure (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate (1:1:1) in crystalline form. Preferably the composition comprises greater than 80% (weight/weight) of (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate (1:1:1) in crystalline form. More preferably greater than 90% (weight/weight) of (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate (1:1:1) in crystalline form. Still more preferably greater than 95% (weight/weight) of (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate (1:1:1) in crystalline form.

In another form, the present invention provides a pharmaceutical composition that includes a compound according to any one of Formulae 1 to 6, or pharmaceutically acceptable salt thereof, and at least one of a pharmaceutically acceptable carrier, diluent or excipient.

In one embodiment the pharmaceutical composition comprises a compound of Formulae 1 to 6 as a neutral compound or zwitterion. In another embodiment the pharmaceutical composition comprises a compound of Formulae 1 to 6 as a pharmaceutically acceptable salt. In yet another embodiment, the pharmaceutical composition comprises a compound of Formulae 1 to 6 as a citrate salt.

In another form, the present invention provides a method of treating a patient in need of treatment for arthritis, more preferably rheumatoid arthritis. The method includes administering to the patient an effective amount of a pharmaceutical composition comprising a compound according to one of Formulae 1 to 6, or a pharmaceutically acceptable salt thereof.

In another form, the present invention provides a method of treating a patient for diabetic nephropathy. The method comprises administering to the patient an effective amount of a compound according to one of Formulae 1 to 6, or a pharmaceutically acceptable salt thereof.

In another form, the present invention provides a method of treating a patient for diabetic nephropathy. The method comprises administering to the patient an effective amount of a pharmaceutical composition compound comprising a compound according to one of Formulae 1 to 6, or a pharmaceutically acceptable salt thereof.

In another form the present invention provides a method of treating a patient for inflammatory bowel disease. The method comprises administering to the patient an effective amount of a pharmaceutical composition compound comprising a compound according to one of Formulae 1 to 6, or a pharmaceutically acceptable salt thereof.

In another form, the present invention provides a method of treating in a patient in need for an autoimmune condition mediated by JAK1 inhibition. The treatment comprises administering to the patient an effective amount of a compound of Formulae 1-6, or a pharmaceutically acceptable salt thereof.

Examples of conditions mediated by JAK1 inhibition and which can be treated according to the present invention include: diabetic nephropathy; Lupus, more preferably systemic Lupus erythematosus; Sjögren's Syndrome; and inflammatory bowel disease, more preferably, Crohn's Disease, and ulcerative colitis.

In another form, the present invention provides a method of treating a patient in need of treatment for arthritis. The method comprises administering to a patient in need an effective amount of a compound according to any one of Formulae 1 to 6, or a pharmaceutically acceptable salt thereof. More preferred methods of treating arthritis include treating a patient for rheumatoid arthritis.

In another form, the present invention provides a method of treating a patient in need of treatment for a condition selected from: diabetic nephropathy; Lupus, more preferably systemic Lupus erythematosus; Sjögren's Syndrome; and inflammatory bowel disease, more preferably, Crohn's Disease and ulcerative colitis. The method comprises administering to the patient an effective amount of a compound according to any one Formulae 1 to 6, or a pharmaceutically acceptable salt thereof.

In another form, the present invention provides a method of treating a patient in need of treatment for cancer. The method comprises administering to a patient in need thereof an effective amount of a compound according to any one of Formulae 1 to 6.

In another form, the present invention provides compound according to any one of Formulae 1 to 6 for use in therapy.

In one embodiment, the therapy, for which the compound according to any one of Formulae 1 to 6 can be used, is selected from: arthritis, more preferably rheumatoid arthritis; diabetic nephropathy; Lupus, more preferably systemic Lupus erythematosus; Sjögren's Syndrome; and inflammatory bowel disease, more preferably Crohn's Disease and ulcerative colitis.

In another form, the present invention provides for the use of a compound according to any one of Formulae 1 to 6 in the manufacture of a medicament.

In one embodiment, the medicament is useful to treat arthritis. In another embodiment, the medicament is useful to treat rheumatoid arthritis. In yet another embodiment, the medicament is useful to treat a condition selected from; diabetic nephropathy; Lupus, more preferably systemic Lupus erythematosus; Sjögren's Syndrome; and inflammatory bowel disease, more preferably, Crohn's Disease and ulcerative colitis. In yet another embodiment, the medicament is useful to treat diabetic nephropathy. In yet another embodiment, the medicament is useful to treat Lupus. In yet another embodiment, the medicament is useful to treat Sjögren's Syndrome. In still yet another embodiment, the medicament is useful to treat inflammatory bowel disease.

The term "pharmaceutically acceptable salt" as used herein refers to a salt of a compound of the invention considered to be acceptable for clinical and/or veterinary use. Examples of pharmaceutically acceptable salts and common methodologies for preparing them can be found in P. Stahl, et al., Handbook of Pharmaceutical Salts: Properties, Selection and Use, 2nd Revised Edition. Wiley-VCH, 2011, and S. M. Berge, et al., "Pharmaceutical Salts," *Journal of Pharmaceutical Sciences*, Vol. 66, No. 1, January 1977.

The pharmaceutical compositions for the present invention may be prepared by procedures known in the art using pharmaceutically acceptable additives. The term "pharmaceutically acceptable additive(s)" as used herein for the pharmaceutical compositions, refers to one or more carriers, diluents, and excipients that are compatible with the other additives of the formulation and not deleterious to the patient. Pharmaceutical compositions and processes for their preparation are known and examples can be found in Loyd, V., et al. eds. Remington: The Science and Practice of Pharmacy 22$^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose and other cellulose derivatives, alginates, gelatin, and polyvinyl-pyrrolidone; kaolin and bentonite; polyethyl glycols.

Preferred pharmaceutical compositions can be formulated as a tablet, capsule, solution for oral administration, or solution for injection. The tablet, capsule, or solution can include a compound of the present invention in an amount effective for treating a patient in need of treatment.

As used herein, the term "effective amount" refers to an amount that is a dosage, which is effective for treating a disorder, such as arthritis, an autoimmune disease or cancer. The attending physician or veterinarian, as one skilled in the art, can readily determine an effective amount by the use of conventional techniques and by observing results obtained under analogous circumstances. A number of factors can be considered to determine the effective amount or dose; the factors, include, but not limited to whether the compound or its salt, will be administered; the co-administration of other agents, if used; the patient's species; its size, age, and general health; the degree of involvement or the severity of the disorder; the response of the individual patient; the mode of administration; the bioavailability characteristics of the preparation administered; the dose regimen selected; the use of other concomitant medication; and other relevant circumstances.

As used herein, the term "patient" refers to a mammal, fowl, or fish. Preferred mammals include a human, a companion mammal, such as a dog or cat or a domesticated animal or livestock, such as a cow, pig, horse, sheep, and goat.

The term "substantially pure" refers to a composition that is greater than 80% pure, more preferably greater than 90% pure, and still more preferably greater than 95% pure on a weight per weight basis.

The compounds of the present invention can be used alone or combined with one or more additional therapeutic agents. For example the compounds of the present invention can be combined with agents for the treatment of inflammation and/or autoimmune diseases. Examples include NSAIDs or COX-2 inhibitors, such as ibuprofen, aspirin, acetaminophen, celecoxib, naproxen, and ketoprofen; opioids, such as oxycodone and fentanyl; methotrexate; and corticosteroids, such as hydrocortisone, prednisolone, and prednisone.

The compounds can also be combined with one or more additional therapeutic agents effective for treating cancers. Examples include cisplatin, carboplatin, etoposide, gemcitabine, paclitaxel, vinorelbine, topotecan, irinotecan, cyclophosphamide, doxorubicin, vincristine, and methotrexate.

The exemplified compounds and the additional therapeutic agent(s) can be administered either together through the same delivery route and device such as a single pill, capsule or tablet; or separately administered either at the same time in separate delivery devices or sequentially.

CHEMISTRY SECTION

The compounds of the present invention, or salts thereof, may be prepared by a variety of procedures, some of which are illustrated in the Preparations, and the Examples below. The product(s) of each step in the procedures below can be recovered by conventional methods, including extraction, evaporation, precipitation, chromatography, filtration, trituration, and crystallization. The reagents and starting materials are readily available to one of ordinary skill in the art. In the preparations described below, the amine substituent can be protected to facilitate the synthesis of the compounds described herein.

As used herein, the following terms have the meanings indicated: "AcOH" refers to glacial acetic acid, "$EC_{50}$" refers to the concentration of an agent which produces 50% response of the target activity compared to a predefined positive control compound (absolute $EC_{50}$); "EtOAc" refers to ethyl acetate; "ES/MS" refers to electrospray mass spectroscopy; "DCM" refers to dichloromethane; DMF" refers to N,N-dimethylformamide; "DMSO" refers to dimethylsulfoxide; "GC-MS" refers to gas chromatography-mass spectrometry; "GFP" refers to green fluorescent protein; "HEPES" refers to 4-(2-hydroxyethyl)-1-piperazineethanesulfonic acid; "hr" or "hrs" refers to hour(s); "$IC_{50}$" refers to the concentration of an agent which produces 50% of the maximal inhibitory response possible for that agent (relative $IC_{50}$), or the concentration of an agent which produces 50% inhibition of the target activity compared to placebo control (absolute $IC_{50}$); "LC-MS" refers to liquid chromatography-mass spectrometry; "MeOH" refers to methanol; "min" refers to minutes; "MS" refers to mass spectroscopy; "MTBE" refers to methyl tert-butyl ether, "OAc" refers to acetate or acetate anion; "QD" refers to once-a-day; "RT or rt" refers to room temperature; "STAT1" refers to signal transducer and activator of transcription 1; "THF" refers to tetrahydrofuran, and "TR-FRET" refers to time-resolved fluorescence energy transfer.

Various amine protecting functionalities are known in the art and include: carbamates such as $C_{1-5}$ alkyl carbamate, $C_{3-6}$ cycloalkyl carbamate, preferably a t-butyl carbamate, (BOC) or benzyl carbamate (CBZ); amides such as $C_{1-3}$ alkylamide, $C_{1-3}$ haloalkylamide, formamide or acetamide chloroacetamide, trifluoridoacetamide; and benzyl amines. Additional examples of amine protecting functionalities, methods of preparing the protected amine substituents, and methods for deprotecting the amine substituents can be found in "Greene's Protective Groups in Organic Synthesis", 5th Ed., Wuts, P. G. M., Eds. John Wiley and Sons, 2014. It will be recognized by those skilled in the art that other functional groups, which can be readily converted to the amine group, can be used. Such functional groups, preparations, and transformations of these groups can be found in "Comprehensive Organic Transformations: A Guide to Functional Group Preparations" by Larock. R. C, Wiley VCH, 1999 and in "March's Advanced Organic Chemistry: Reactions, Mechanisms and Structure" Smith, M. B., Wiley-Interscience, 7th Ed., 2013.

Preparation 1

(2R)-2-(Trifluoromethyl)oxirane

Add acetic acid (0.89 mL, 0.052 eq) to a solution of (1S,2S)-(+)-1,2-cyclohexanediamino-N,N'-bis(3,5-di-t-butylsalicylidene)cobalt (II) (0.90 g, 0.0050 eq) in toluene (16.65 mL). Stir at rt for 30 min. Remove the solvent in vacuo. Add toluene (20 mL) and concentrate in vacuo. Cool to 0° C. and add 2-(trifluoromethyl)oxirane (37.00 g, 330 mmol; 80.0% ee, (2R) is the major enantiomer). Stir for five minutes and add water (0.80 mL, 0.15 eq) dropwise. Slowly warm to rt and stir overnight. Vacuum distill at rt, and collect the title compound in a cooled flask as a light yellow oil (28.10 g, 76%; 99.8% ee). $^1$H NMR (CDCl$_3$) δ 2.92-2.94 (m, 1H), 2.98-3.01 (m, 1H), 3.41-3.46 (m, 1H).

Combine the title compound (0.13 g, 1.16 mmol) and MeOH (1.3 mL). Cool to 0° C., and add triethylamine (0.17 mL, 1.10 eq) and thiophenol (0.12 mL, 1.05 eq). Stir the mixture for 30 min. Monitor the reaction via GC-MS for the formation of 1,1,1-trifluoro-3-phenylsulfanyl-propan-2-ol; m/z=222. Analysis of the product via chiral LC-MS reveals that the isomeric purity of the product is 99.8% ee, (2S)-1,1,1-trifluoro-3-phenylsulfanyl-propan-2-ol is the major enantiomer.

Preparation 2

1-Bromo-3,5-difluoro-2-nitrobenzene

Add nitric acid (fuming, 20 mL) drop-wise to a solution of 1-bromo-3,5-difluorobenzene (35.00 mL, 304 mmol) in sulfuric acid (50 mL) at 0° C. Slowly warm to rt and stir overnight. Pour the reaction mixture into a mixture of ice and water (600 mL). Slowly warm to rt. Add EtOAc (200 mL) and hexanes (100 mL). Stir until all the solids dissolve. Separate the layers. Wash the organic layer with saturated aqueous sodium chloride, dry over Na$_2$SO$_4$, filter, and concentrate the filtrate in vacuo to give the title compound as a yellow oil (57.37 g, 79%). GC-MS m/z=($^{79}$Br/$^{81}$Br) 237, 239 (M+H).

Preparation 3

3-Bromo-5-fluoro-N-methyl-2-nitroaniline

Add 2 M monomethylamine in tetrahydrofuran (92 mL, 2.00 eq) to a solution of 1-bromo-3,5-difluoro-2-nitrobenzene (21.90 g, 92 mmol) in 1,4-dioxane (92 mL). Stir at rt for 45 min. Add water; then extract with EtOAc. Collect the organic extracts and wash with saturated aqueous sodium chloride. Dry over anhydrous Na$_2$SO$_4$, filter, and concentrate the filtrate in vacuo to provide a residue. Subject the residue to normal phase chromatography, eluting with a 20-40% DCM in hexanes gradient, to give the title compound as an orange solid (16.95 g, 74%). MS (ES) m/z=($^{79}$Br/$^{81}$Br) 249/251 (M+H).

Preparation 4 tert-Butyl {cis-4-[3-bromo-5-(methylamino)-4-nitrophenoxy]cyclohexyl}carbamate

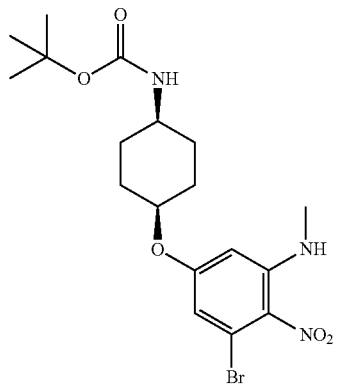 [SMILES: CNc1cc(O[C@H]2CC[C@@H](NC(=O)OC(C)(C)C)CC2)cc(Br)c1[N+](=O)[O-]]

Combine 3-bromo-5-fluoro-N-methyl-2-nitroaniline (75.04 g, 301 mmol), tert-butyl (cis-4-hydroxycyclohexyl)carbamate (89.52 g, 1.38 eq), tetra(n-butyl)ammonium bisulfate (15.58 g, 0.15 eq) in DCM (975 mL) and 5 M aqueous sodium hydroxide (241 mL). Stir rapidly at 37° C. under nitrogen for five days. Cool to rt. Dilute with DCM (200 mL) and water (400 mL). Separate the layers. Extract the aqueous with DCM (3×100 mL). Wash the combined organic extracts with saturated aqueous sodium chloride, dry over anhydrous Na$_2$SO$_4$, filter, and concentrate the filtrate in vacuo to provide a residue. Subject the residue to normal phase chromatography, eluting with a 0-40% EtOAc in hexanes gradient, to give the title compound as an orange solid (68.57 g, 51%). MS (ES) m/z=($^{79}$Br/$^{81}$Br) 442/444 (M–H).

Preparation 5 tert-Butyl {cis-4-[(4-bromo-1-methyl-1H-benzimidazol-6-yl)oxy]cyclohexyl}carbamate

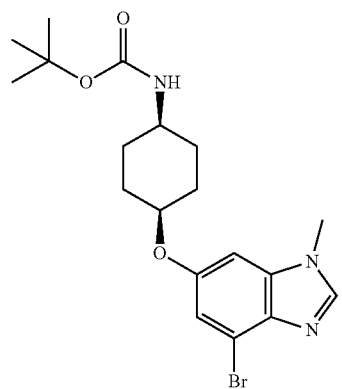 [SMILES: Cn1cnc2c(Br)cc(O[C@H]3CC[C@@H](NC(=O)OC(C)(C)C)CC3)cc21]

Combine tert-butyl {cis-4-[3-bromo-5-(methylamino)-4-nitrophenoxy]cyclohexyl}carbamate (76.92 g, 173 mmol) and platinum (5% on carbon sulfided, 3.85 g) in tetrahydrofuran (923 mL) in a Parr® reactor. Stir at rt under H$_2$ (414 kPa) for three days. Filter through diatomaceous earth. Wash the diatomaceous earth with THF. Add trimethylorthoformate (165 mL, 8.70 eq) to the combined THF filtrates. Stir for 22 hours at 63° C. Concentrate the majority of the reaction mixture in vacuo. Dilute with water (400 mL) and EtOAc (400 mL). Basify with aqueous sodium carbonate to adjust the pH to 9. Separate the layers. Extract the aqueous with EtOAc (2×200 mL). Dry the combined organic extracts over anhydrous Na$_2$SO$_4$, filter, and concentrate the filtrate in vacuo. Dilute the residue with methyl tert-butyl ether (400 mL) and sonicate for 30 minutes. Filter, wash with methyl tert-butyl ether, and dry under vacuum to give the title compound as a light brown solid (52.02 g, 71%). MS (ES) m/z=($^{79}$Br/$^{81}$Br) 424/426 (M+H).

Preparation 6 cis-4-[(4-Bromo-1-methyl-1H-benzimidazol-6-yl)oxy]cyclohexanamine

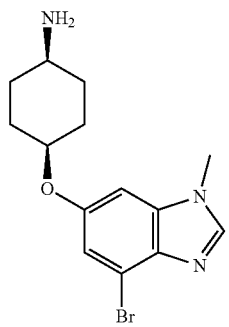 [SMILES: Cn1cnc2c(Br)cc(O[C@H]3CC[C@@H](N)CC3)cc21]

Add trifluoroacetic acid (666 mL) slowly to a solution of tert-butyl {cis-4-[(4-bromo-1-methyl-1H-benzimidazol-6-yl)oxy]cyclohexyl}carbamate (222 g, 497 mmol) in DCM (1110 mL) at 0° C. Slowly warm the mixture to rt and stir overnight. Concentrate the mixture in vacuo. Add water (250 mL) and basify with 50% aqueous sodium hydroxide to adjust the pH to 10. Extract with 20% MeOH in DCM (1500 mL, then 500 mL, then 250 mL). Wash the combined organic extracts with 2 M aqueous sodium hydroxide, dry over anhydrous $MgSO_4$, filter, and concentrate the filtrate to give the title compound as a brown solid (155 g, 91%). MS (ES) m/z=($^{79}$Br/$^{81}$Br) 324/326 (M+H).

Preparation 7

(2R)-3-({cis-4-[(4-Bromo-1-methyl-1H-benzimidazol-6-yl)oxy]cyclohexyl}amino)-1,1,1-trifluoropropan-2-ol

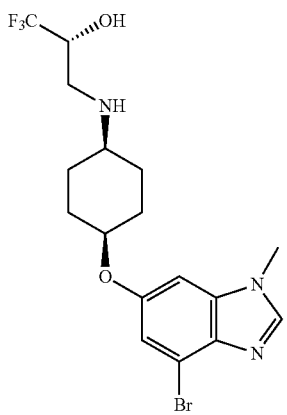 [SMILES: Cn1cnc2c(Br)cc(O[C@H]3CC[C@@H](NC[C@@H](O)C(F)(F)F)CC3)cc21]

Add (2R)-2-(trifluoromethyl)oxirane (73.29 g, 1.50 eq) to a solution of cis-4-[(4-bromo-1-methyl-1H-benzimidazol-6-yl)oxy]cyclohexanamine (150.4 g, 436 mmol) in MeOH (1053 mL). Stir at rt overnight. Concentrate the reaction mixture in vacuo to provide a residue. Subject the residue to normal phase chromatography, eluting with a 0-10% EtOH in DCM gradient, to give the title compound as an off-white solid (98.10 g, 52%). MS (ES) m/z=($^{79}$Br/$^{81}$Br) 436/438 (M+H).

Preparation 8

1-(3-Methoxypropyl)-5-methyl-3-nitro-1H-pyrazole

Add acetonitrile (56 mL) to a mixture of 5-methyl-3-nitro-1H-pyrazole (3.0 g, 22 mmol), potassium carbonate (6.2 g, 2.0 eq), and 1-bromo-3-methoxypropane (3.8 g, 1.1 eq). Stir at 65° C. overnight. Cool to rt. Add EtOAc (~50 mL) and filter. Concentrate the filtrate in vacuo. Subject the residue to normal phase chromatography, eluting with 35% EtOAc in hexanes, to give the title compound (3.3 g, 70%). MS (ES) m/z=200 (M+H).

Preparation 9

1-(3-Methoxypropyl)-5-methyl-1H-pyrazol-3-amine

Add palladium on charcoal (5% w/w, 0.38 g) to a 500 mL Parr® reactor. Purge reactor with $N_2$ and add EtOH (100 mL). Add a solution of 1-(3-methoxypropyl)-5-methyl-3-nitro-1H-pyrazole (3.3 g, 17 mmol) in EtOH (100 mL). Stir at rt under $H_2$ (60 psi) for two hours. Filter through diatomaceous earth. Concentrate the filtrate in vacuo to give the title compound as an orange oil (2.7 g, 96%). MS (ES) m/z=170 (M+H).

Preparation 10

1-(2-Methoxyethyl)-5-methyl-3-nitro-1H-pyrazole

Add acetonitrile (35 mL) to a mixture of 5-methyl-3-nitro-1H-pyrazole (0.95 g, 7.1 mmol), potassium carbonate (2.0 g, 2.0 eq), and 1-bromo-2-methoxyethane (2.0 mL, 3.0 eq). Stir at 75° C. for three hours. Cool to rt. Add diethyl ether (~35 mL) and filter. Rinse the solids with EtOAc (2×25 mL). Concentrate the filtrate in vacuo to provide a residue. Subject the residue to normal phase chromatography, eluting with a 0-100% EtOAc in hexanes gradient, to give the title compound as a yellow oil (1.1 g, 64%). MS (ES) m/z=186 (M+H).

Preparation 11

1-(2-Methoxyethyl)-5-methyl-1H-pyrazol-3-amine

Add palladium on charcoal (10% w/w, 0.38 g) to a flask. Purge with $N_2$ and add EtOH (10 mL). Add a solution of 1-(2-methoxyethyl)-5-methyl-3-nitro-1H-pyrazole (0.86 g, 4.6 mmol) in EtOH (40 mL). Stir at rt under $H_2$ (balloon) overnight. Filter through diatomaceous earth. Concentrate the filtrate in vacuo to give the title compound as a brown oil (0.68 g, 84%). MS (ES) m/z=156 (M+H).

Preparation 12

1-(5-Methyl-3-nitro-1H-pyrazol-1-yl)propan-2-ol

Add acetonitrile (75 mL) to a mixture of 5-methyl-3-nitro-1H-pyrazole (2.0 g, 15 mmol), potassium carbonate (4.1 g, 2.0 eq), and 1-chloro-2-propanol (3.8 mL, 3.0 eq). Stir at 85° C. overnight. Cool to rt. Filter and rinse the solids with EtOAc. Concentrate the filtrate in vacuo to provide a residue. Subject the residue to normal phase chromatography, eluting with 50% EtOAc in hexanes, to give the title compound (2.0 g, 65%). MS (ES) m/z=186 (M+H).

Preparation 13

1-(3-Amino-5-methyl-1H-pyrazol-1-yl)propan-2-ol

Add palladium on charcoal (10% w/w, 0.35 g) to a flask. Purge with $N_2$ and add EtOH (50 mL). Add a solution of 1-(5-methyl-3-nitro-1H-pyrazol-1-yl)propan-2-ol (2.0 g, 11 mmol) in EtOH (150 mL). Stir at rt under $H_2$ (balloon) overnight. Filter through diatomaceous earth. Concentrate the filtrate in vacuo to give the title compound as a pink oil (1.2 g, 69%). MS (ES) m/z=156 (M+H).

Preparation 14

(2S)-1-(5-Methyl-3-nitro-1H-pyrazol-1-yl)propan-2-ol

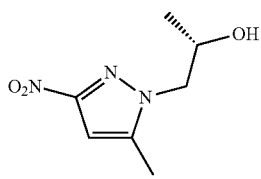

Add acetonitrile (45 mL) to a mixture of 5-methyl-3-nitro-1H-pyrazole (1.2 g, 9.0 mmol), potassium carbonate (2.5 g, 2.0 eq), and (S)-1-chloro-2-propanol (0.98 g, 1.2 eq). Stir at 85° C. for four days. Cool to rt. Filter to collect the solid and rinse the solid with EtOAc, then discard the solid. Collect and concentrate the filtrate in vacuo to provide a residue. Subject the residue to normal phase chromatography, eluting with 50% EtOAc in hexanes, to give the title compound as a white solid (1.1 g, 67%). MS (ES) m/z=186 (M+H).

Preparation 15

(2S)-1-(3-Amino-5-methyl-1H-pyrazol-1-yl)propan-2-ol

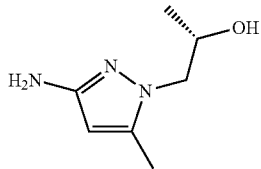

Add palladium on charcoal (10% w/w, 0.22 g) to a flask. Add a solution of (2S)-1-(5-methyl-3-nitro-1H-pyrazol-1-yl)propan-2-ol (1.1 g, 6.0 mmol) in EtOH (50 mL). Stir at rt under $H_2$ (balloon) overnight. Filter through diatomaceous earth. Wash the solids with MeOH. Concentrate the filtrate in vacuo to give the title compound (0.89 g, 95%). MS (ES) m/z=156 (M+H).

Preparation 16

(2R)-1-(5-Methyl-3-nitro-1H-pyrazol-1-yl)propan-2-ol

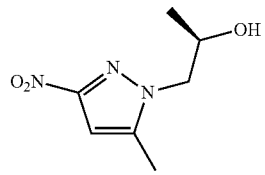

Add acetonitrile (41 mL) to a mixture of 5-methyl-3-nitro-1H-pyrazole (1.1 g, 8.2 mmol), potassium carbonate (2.3 g, 2.0 eq), and (R)-1-chloro-2-propanol (0.92 mL, 1.3 eq). Stir at 85° C. overnight. Cool to rt. Filter and rinse the solids with EtOAc. Concentrate the filtrate in vacuo to provide a residue. Subject the residue to normal phase chromatography, eluting with 50% EtOAc in hexanes, to give the title compound as a white solid (0.74 g, 48%). MS (ES) m/Z=186 (M+H).

Preparation 17

(2R)-1-(3-Amino-5-methyl-1H-pyrazol-1-yl)propan-2-ol

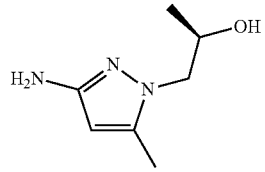

Add palladium on charcoal (10% w/w, 0.15 g) to a flask. Add a solution of (2R)-1-(5-methyl-3-nitro-1H-pyrazol-1-yl)propan-2-ol (0.74 g, 4.0 mmol) in EtOH (33 mL). Stir at rt under $H_2$ (balloon) overnight. Filter through diatomaceous earth. Wash the solids with MeOH. Concentrate the filtrate in vacuo to give the title compound as a yellow solid (0.58 g, 95%). MS (ES) m/z=156 (M+H).

Preparation 18

Ethyl 8-methyl-1,4-dioxaspiro[4.5]decane-8-carboxylate

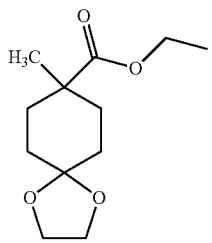

Combine diisopropylamine (55 mL, 1.36 eq) and 2-methyltetrahydrofuran (500 mL). Cool to −20° C. under $N_2$. Add 2.5 M n-butyllithium in hexanes (150 mL, 1.30 eq) dropwise over 10 min, then stir the solution for at −20° C. for an additional 15 min. Transfer the solution via cannula over 20 min to a solution of ethyl 1,4-dioxaspiro[4.5]decane-8-carboxylate (50 mL, 287 mmol) in 2-methyltetrahydrofuran (500 mL) at −40° C. Stir the solution at −40° C. for ten min. Add a solution of iodomethane (30 mL, 1.68 eq) in 2-methyltetrahydrofuran (60 mL) dropwise over ten min. Stir at −40° C. for one hr. Allow to slowly warm to rt and stir overnight. Quench with saturated aqueous ammonium chloride (150 mL). Separate the layers. Extract the aqueous layer with methyl tert-butyl ether (50 mL). Dry the combined organic layers over anhydrous Na$_2$SO$_4$, filter, and concentrate in vacuo to give the title compound as a yellow oil (63.3 g, 97%). $^1$H NMR (CDCl3) δ 1.16 (s, 3H), 1.20-1.25 (m, 3H), 1.42-1.66 (m, 6H), 2.07-2.14 (m, 2H), 3.91 (s, 4H), 4.08-4.15 (m, 2H).

Preparation 19

8-Methyl-1,4-dioxaspiro[4.5]decane-8-carboxylic Acid

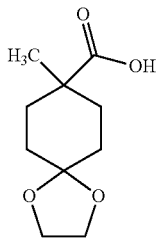

Combine ethyl 8-methyl-1,4-dioxaspiro[4.5]decane-8-carboxylate (20 g, 88 mmol), MeOH (100 mL), and 3 M sodium hydroxide in water (140 mL). Heat the reaction mixture at reflux overnight. Concentrate in vacuo and dilute with water (150 mL) and methyl tert-butyl ether (50 mL). Separate the layers and discard the organic layer. Acidify the aqueous layer with 3% w/w aqueous hydrochloric acid to adjust pH to 2. Extract with methyl tert-butyl ether (3×100 mL). Dry the combined organics over anhydrous Na$_2$SO$_4$, filter, and concentrate in vacuo to give the title compound as a yellow oily solid (12.6 g, 72%). $^1$H NMR (CDCl3) δ 1.25 (s, 3H), 1.47-1.60 (m, 2H), 1.65-1.70 (m, 4H), 2.08-2.17 (m, 2H), 3.93 (s, 4H).

Preparation 20

Prop-2-en-1-yl (8-methyl-1,4-dioxaspiro[4.5]dec-8-yl)carbamate

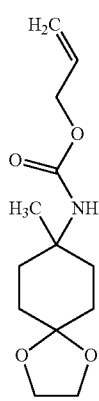 [SMILES: C=CCOC(=O)NC1(C)CCC2(CC1)OCCO2]

Combine 8-methyl-1,4-dioxaspiro[4.5]decane-8-carboxylic acid (12 g, 60 mmol) and acetonitrile (200 mL). Add triethylamine (25.5 mL, 3.11 eq) and diphenylphosphoryl azide (15 mL, 1.18 eq). Stir at rt under N$_2$ for two hours. Add allyl alcohol (25 mL, 6.25 eq). Stir the reaction mixture at reflux overnight. Concentrate in vacuo and dilute with water (150 mL) and methyl tert-butyl ether (150 mL). Separate the layers. Extract the aqueous layer with methyl tert-butyl ether (2×100 mL). Dry the combined organics over anhydrous Na$_2$SO$_4$, filter, and concentrate in vacuo to give the title compound as a brown oil (10.8 g, 71%). $^1$H NMR (CDCl3) δ 1.34 (s, 3H), 1.57-1.69 (m, 6H), 1.98-2.11 (m, 2H), 3.92-3.93 (m, 4H), 4.48-4.66 (m, 3H), 5.16-5.32 (m, 2H), 5.82-5.99 (m, 1H).

Preparation 21

Prop-2-en-1-yl (1-methyl-4-oxocyclohexyl)carbamate

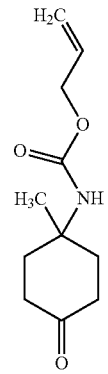

Combine prop-2-en-1-yl (8-methyl-1,4-dioxaspiro[4.5]dec-8-yl)carbamate (10.5 g, 41 mmol), acetone (30 mL), and water (3 mL). Add 35% hydrochloric acid (2.7 mL). Stir at rt overnight. Concentrate the reaction mixture in vacuo to remove the acetone. Dilute with methyl tert-butyl ether (100 mL). Basify with 6 M aqueous potassium carbonate to adjust pH to 8. Separate the layers. Extract the aqueous layer with methyl tert-butyl ether (2×20 mL). Dry the combined organics over anhydrous Na$_2$SO$_4$, filter, and concentrate in vacuo to provide a residue. Subject the residue to normal phase chromatography, eluting with a gradient of 20-100% methyl tert-butyl ether in hexanes to give the title compound as a colorless oil (6.0 g, 69%). $^1$H NMR (CDCl3) δ 1.44 (s, 3H), 1.76-1.88 (m, 2H), 2.24-2.51 (m, 6H), 4.54 (d, 2H), 4.78 (s, 1H), 5.20-5.35 (m, 2H), 5.85-6.00 (m, 1H).

Preparation 22

Prop-2-en-1-yl (cis-4-hydroxy-1-methylcyclohexyl)carbamate

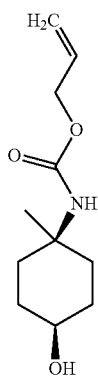

Add 0.1 M monopotassium phosphate buffer (pH 7, 500 mL), MgSO$_4$ (0.12 g), NADP (0.27 g), and ketoreductase-P1-B10 (0.32 g) to a solution of prop-2-en-1-yl (1-methyl-4-oxocyclohexyl)carbamate (32.8 g, 155 mmol) in isopropanol (110 mL). Stir at 35° C. for 24 hours. Extract with EtOAc. Dry the organics over anhydrous MgSO$_4$, filter, and concentrate the filtrate in vacuo to give the title compound as a yellow oil (32.41 g, 98%). $^1$H NMR (CDCl3) δ 1.18-1.50 (m, 7H), 1.57-1.88 (m, 3H), 1.98-2.14 (m, 2H), 3.55-3.65 (m, 1H), 4.46-4.66 (m, 3H), 5.17-5.32 (m, 2H), 5.83-5.96 (m, 1H). The proton multiplet at 3.55-3.65 ppm is known to be in the cis configuration.

Preparation 23

Prop-2-en-1-yl {cis-4-[(4-bromo-1-methyl-1H-benzimidazol-6-yl)oxy]-1-methylcyclohexyl}carbamate

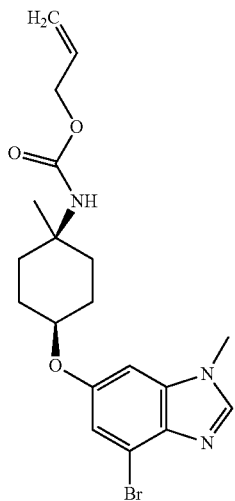 [SMILES: C=CCOC(=O)N[C@]1(C)CC[C@H](Oc2cc(Br)c3ncn(C)c3c2)CC1]

Add 5 M aqueous sodium hydroxide (270 mL) and tetra(n-butyl)ammonium bisulfate (7.50 g, 0.18 eq) to a solution of 3-bromo-5-fluoro-N-methyl-2-nitroaniline (30.00 g, 120 mmol) and prop-2-en-1-yl (cis-4-hydroxy-1-methylcyclohexyl)carbamate (33.00 g, 1.28 eq) in DCM (300 mL). Stir the mixture rapidly at rt for 24 hours. Add tetrabutylammonium hydrogen sulfate (7.50 g, 0.18 eq). Stir rapidly at rt overnight. Dilute with water (20 mL). Separate the layers. Extract the aqueous layer with DCM (2×150 mL). Wash the combined organic extracts with 5% w/w aqueous sodium chloride (200 mL) and water (200 mL); then concentrate the organic extracts in vacuo. Combine the concentrated organic extracts and acetic acid (650 mL). Add trimethylorthoformate (45 mL). Stir at 90° C. for 2.5 hrs under nitrogen. Dilute with EtOAc (500 mL). Filter through a pad of diatomaceous earth. Wash the pad with EtOAc. Concentrate the combined filtrates in vacuo. Dilute with 2 M aqueous dipotassium phosphate (60 mL) and 2-methyltetrahydrofuran (60 mL). Stir for 20 min, then filter through diatomaceous earth. Separate the layers. Extract the aqueous layer with 2-methyltetrahydrofuran (2×20 mL). Combine the organic extracts, wash with water, and concentrate in vacuo. Dilute with 1-methyl-2-pyrrolidinone (100 mL) and stir to obtain a homogenous mixture. Dropwise add the mixture to water (1200 mL) over 30 min. Stir for 30 min, filter to collect the solid, and wash the solid with water. Dissolve the solid in 2-methyltetrahydrofuran (250 mL) and concentrate in vacuo. Dilute the solution with isopropanol (3×150 mL) and concentrate in vacuo. Dilute the solution with 2-methyltetrahydrofuran (10 mL) and concentrate in vacuo to give the title compound as an oily, brown residue (31.5 g, 74%). MS (ES) m/z=($^{79}$Br/$^{81}$Br) 422/424 (M+H).

Preparation 24 cis-4-[(4-Bromo-1-methyl-1H-benzimidazol-6-yl)oxy]-1-methylcyclohexanamine

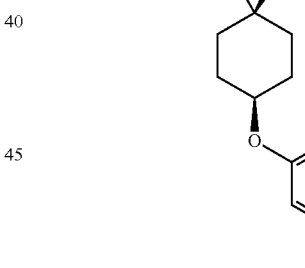

Combine prop-2-en-1-yl {cis-4-[(4-bromo-1-methyl-1H-benzimidazol-6-yl)oxy]-1-methylcyclohexyl}carbamate (30 g, 71 mmol), bis(dibenzylideneacetone)palladium (0.50 g, 0.017 eq), 1,4-bis(diphenylphosphino)butane (0.50 g, 0.022 eq), and thiosalicylic acid (15 g, 1.90 eq) in 2-methyltetrahydrofuran (700 mL). Heat the reaction mixture at 50° C. for one hour. Dilute with water (300 mL) and methyl tert-butyl ether (300 mL). Acidify with 35% hydrochloric acid to adjust pH to 2. Separate the layers and discard the organic layer. Dilute the aqueous layer with EtOAc (20 mL) and stir for ten min. Separate the layers and discard the organics. Dilute the aqueous layer with DCM (150 mL) and stir for ten min. Separate the layers and discard the organic layer. Basify the aqueous layer with sodium hydroxide. Filter; collect the solid; then subject the resulting solid to normal phase chromatography, eluting with 5% 2 M ammoniated MeOH in DCM, to give the title compound (12.0 g, 50%). MS (ES) m/z=($^{79}$Br/$^{81}$Br) 338/340 (M+H).

Preparation 25

(2R)-3-({cis-4-[(4-Bromo-1-methyl-1H-benzimidazol-6-yl)oxy]-1-methylcyclohexyl}amino)-1,1,1-trifluoropropan-2-ol

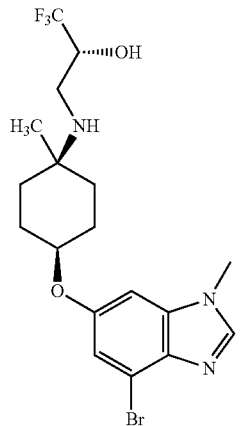 [SMILES: Cn1cnc2c(Br)cc(O[C@H]3CC[C@@](C)(NC[C@@H](O)C(F)(F)F)CC3)cc21]

Combine cis-4-[(4-bromo-1-methyl-1H-benzimidazol-6-yl)oxy]-1-methylcyclohexanamine (11.6 g, 34 mmol), (2R)-2-(trifluoromethyl)oxirane (4.00 g, 1.05 eq), EtOH (45 mL), and water (45 mL) in a glass pressure reactor. Seal and heat the reaction mixture at 90° C. for one hr. Allow to cool to rt. Add (2R)-2-(trifluoromethyl)oxirane (0.44 g, 0.12 eq). Seal and heat the reaction mixture at 90° C. for one hr. Concentrate in vacuo. Dilute with water (100 mL), methyl tert-butyl ether (20 mL) and EtOAc (20 mL). Acidify with 35% aqueous hydrochloric acid to adjust pH to 2 and stir until a complete solution is achieved. Separate the layers and discard the organic layer. Dilute the aqueous layer with methyl tert-butyl ether (40 mL). Separate the layers and discard the organic layer. Basify the aqueous layer with 50% w/w aqueous sodium hydroxide to adjust pH to 10. Extract the aqueous layer with EtOAc (2×50 mL). Combine the organic extracts and concentrate in vacuo. Crystallize a solid from EtOAc (50 mL). Filter to collect the solid, then wash the resulting solid with EtOAc to give the title compound as a white solid (6.3 g, 41%). MS (ES) m z=($^{79}$Br/$^{81}$Br) 450/452 (M+H).

Concentrate the filtrate from the crystallization mother liquor to provide a residue. Subject the residue to normal phase chromatography, eluting with 5% 2 M ammoniated MeOH in EtOAc, to give additional title compound as an off-white solid (3.3 g, 21%). MS (ES) m/z=($^{79}$Br/$^{81}$Br) 450/452 (M+H).

Preparation 26

(2R)-2-(Difluoromethyl)-1,4-dioxaspiro[4.5]decane

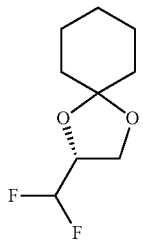

Dissolve (3R)-1,4-dioxaspiro[4.5]decane-3-carbaldehyde (15.98 g, 89.19 mmol) in DCM (80 mL). Place under N$_2$ and cool the solution to 0° C. Cautiously add diethylaminosulfur trifluoride (15 mL, 1.2 eq) dropwise. Allow to slowly warm to rt and stir overnight. Slowly pour the mixture into a stirring mixture of crushed ice, saturated aqueous sodium bicarbonate, and DCM. Add dipotassium phosphate (5 g) and portion-wise additions of potassium carbonate, maintaining pH ~7-8, until no more bubbling is observed. Stir for 20 min. Separate the layers. Extract the aqueous layer with DCM (3×). Wash the combined organic extracts with 1M aqueous sodium bisulfite and saturated aqueous sodium chloride. Dry the organics over anhydrous Na$_2$SO$_4$, filter, and concentrate the filtrate in vacuo to give the title compound as an amber oil (17.37 g, 93%). GC-MS m/z=192.

Preparation 27

(2R)-3,3-Difluoro-2-hydroxypropyl 4-methylbenzenesulfonate

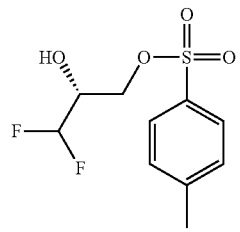 [SMILES: Cc1ccc(S(=O)(=O)OC[C@@H](O)C(F)F)cc1]

Dissolve (2R)-2-(difluoromethyl)-1,4-dioxaspiro[4.5]decane (9.08 g, 47.2 mmol) in MeOH (250 mL). Add p-toluenesulfonic acid monohydrate (0.70 g, 0.1 eq). Stir at rt for one week. Add sodium bicarbonate (0.60 g). Stir for one hr. Add silica gel and trimethylamine (3 mL). Stir for ten min. Concentrate in vacuo and purify by normal phase chromatography, eluting with a 15-100% EtOAc in hexanes gradient, to give (2R)-3,3-difluoropropane-1,2-diol as a yellow oil (2.95 g).

Dissolve (2R)-3,3-difluoropropane-1,2-diol (2.0 g, 15.2 mmol) in DCM (40 mL). Place under nitrogen and cool the solution to 0° C. Add 2,6-lutidine (8.0 mL, 4.5 eq). Add p-toluenesulfonyl chloride (3.0 g, 1.0 eq) portion-wise. Allow to slowly warm to rt and stir for two days. Cool to −78° C. and add trimethylsilyl trifluoromethanesulfonate (1.5 mL, 0.5 eq) dropwise. Allow to warm to 0° C. over 40 min. Add trimethylsilyl trifluoromethanesulfonate (1.5 mL, 0.5 eq) dropwise. Stir for 30 min and quench with MeOH (5 mL). Dilute with DCM and add a solution of sodium phosphate (4.9 g) in water (75 mL). Adjust the pH to ~3 with 2M aqueous potassium bisulfate. Separate the layers. Extract the aqueous layer with diethyl ether. Dry the organic extracts over anhydrous Na₂SO₄, filter, and concentrate the filtrate in vacuo. Add ethylene glycol (1 mL) and silica gel (~20 g). Concentrate in vacuo to provide a residue. Subject the residue to normal phase chromatography, eluting with a 20-100% B in A gradient (A: hexanes, B: 6:3:1 hexanes: DCM:THF), to give the title compound (1.37 g, 16%). GC-MS m/z=266.

Preparation 28

6-[(cis-4-Aminocyclohexyl)oxy]-N-(1,5-dimethyl-1H-pyrazol-3-yl)-1-methyl-1H-benzimidazol-4-amine

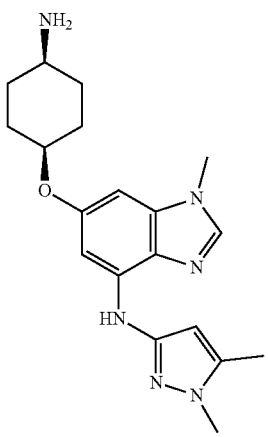 [SMILES: Cc1cc(Nc2cc(O[C@H]3CC[C@@H](N)CC3)cc3c2ncn3C)nn1C]

Combine cis-4-[(4-bromo-1-methyl-1H-benzimidazol-6-yl)oxy]cyclohexanamine (25.70 g, 79.27 mmol), 1,5-dimethyl-1H-pyrazol-3-amine (9.08 g, 1.0 eq), potassium carbonate (28.48 g, 2.6 eq), 2-(dicyclohexylphosphino)3,6-dimethoxy-2',4',6'-triisopropyl-1,1'-biphenyl (8.60 g, 0.20 eq), tris(dibenzylideneacetone)dipalladium(0) (3.63 g, 0.050 eq), and acetic acid (0.14 mL) in tert-butyl alcohol (250 mL). Heat at reflux overnight. Concentrate the reaction mixture in vacuo. Add DCM and water; separate the layers. Dry the organics over anhydrous magnesium sulfate, filter, and concentrate in vacuo. Triturate from EtOAc and hexanes to give a tan solid. Subject the tan solid to normal phase chromatography, eluting with hexanes, then 5% MeOH in DCM, then 20% 2M ammoniated MeOH in DCM, to give the title compound as a tan solid (21.71 g, 77%). MS (ES) m/z=355 (M+H).

Preparation 29

2-(3-Nitro-1H-pyrazol-1-yl)pyridine

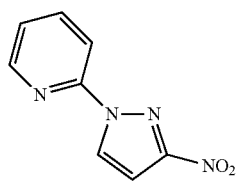 [SMILES: O=[N+]([O-])c1ccn(-c2ccccn2)n1]

In each of two separate vials, combine 3-nitro-1H-pyrazole (3.0 g, 27 mmol), 2-fluoropyridine (2.9 mL, 1.3 eq), and triethylamine (4.6 mL, 1.2 eq) in 1-methyl-2-pyrrolidinone (20 mL). Seal and stir at 180° C. overnight. Cool to rt. Combine the reaction mixtures and dilute with water. Filter to collect a solid, wash the solid with water, and dry under vacuum to give the title compound (5.9 g, 58%). MS (ES) m/z=191 (M+H).

Preparation 30

1-Pyridin-2-yl-1H-pyrazol-3-amine

Add palladium on charcoal (10% w/w, 1.9 g) to a flask. Purge with N₂ and add EtOH (200 mL). Add 2-(3-nitro-1H-pyrazol-1-yl)pyridine (2.5 g, 13 mmol). Stir at rt under H₂ (balloon) overnight. Add a small amount of diatomaceous earth and stir for five min. Filter through a pad of diatomaceous earth and wash the pad with EtOH. Concentrate the filtrate in vacuo to give the title compound as a brown solid (1.8 g, 85%). MS (ES) m/z=161 (M+H).

Preparation 31

1-(Methylsulfonyl)-3-nitro-1H-pyrazole

Combine 3-nitro-1H-pyrazole (3.0 g, 27 mmol), methanesulfonyl chloride (2.5 mL, 1.2 eq), and triethylamine (4.4 mL, 1.2 eq) in DCM (20 mL). Stir at rt for two hours. Dilute with DCM and saturated aqueous sodium bicarbonate. Separate the layers. Wash the organic layer with water and brine. Dry the organic layer over anhydrous MgSO₄, filter, and concentrate the filtrate in vacuo to give the title compound as a brown solid (3.7 g, 73%). ¹H NMR (DMSO-d6) δ 3.74 (s, 3H), 7.30 (d, J=2.9 Hz, 1H), 8.55 (d, J=2.9 Hz, 1H).

Preparation 32

3-Nitro-1-tetrahydro-2H-pyran-3-yl-1H-pyrazole

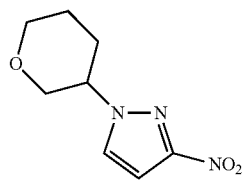 [SMILES: O=[N+]([O-])c1ccn(C2CCCOC2)n1]

Combine tetrahydropyran-3-ol (1.3 g, 13 mmol), 1-(methylsulfonyl)-3-nitro-1H-pyrazole (2.4 g, 1.0 eq), and cesium carbonate (4.8 g, 1.2 eq) in acetonitrile (40 mL). Stir at 90° C. overnight. Concentrate the mixture in vacuo. Dilute with EtOAc and filter through a pad of diatomaceous earth. Concentrate the filtrate in vacuo to provide a residue. Subject the residue to C-18 reverse phase chromatography eluting with a gradient from 0% to 100% of (0.1% formic acid in acetonitrile) in (0.1% formic acid in water), to give the title compound (0.35 g, 14%). MS (ES) m/z=198 (M+H).

Preparation 33

1-(Tetrahydro-2H-pyran-3-yl)-1H-pyrazol-3-amine

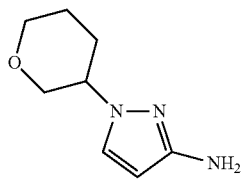 [SMILES: Nc1ccn(C2CCCOC2)n1]

Add palladium on charcoal (10% w/w, 0.10 g) to a flask. Purge with $N_2$ and add EtOH (20 mL). Add 3-nitro-1-tetrahydro-2H-pyran-3-yl-1H-pyrazole (0.30 g, 1.5 mmol). Stir at rt under $H_2$ (balloon) for two hrs. Filter through diatomaceous earth and wash with EtOH. Concentrate the filtrate in vacuo to give the title compound as a gray solid (0.24 g, 94%). MS (ES) m/z=168 (M+H).

Example 1

(2R)-1,1,1-Trifluoro-3-({cis-4-[(4-{[1-(3-methoxy-propyl)-5-methyl-1H-pyrazol-3-yl]amino}-1-methyl-1H-benzimidazol-6-yl)oxy]cyclohexyl}amino)propan-2-ol

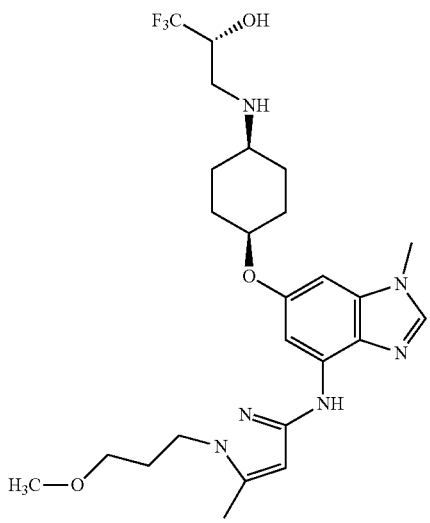 [SMILES: COCCCN/C(C)=C\C(=N)Nc1cc(O[C@H]2CC[C@@H](NC[C@@H](O)C(F)(F)F)CC2)cc2c1ncn2C]

Combine (2R)-3-({cis-4-[(4-bromo-1-methyl-1H-benzimidazol-6-yl)oxy]cyclohexyl}amino)-1,1,1-trifluoropropan-2-ol (4.0 g, 9.2 mmol), 1-(3-methoxypropyl)-5-methyl-1H-pyrazol-3-amine (2.2 g, 1.4 eq), potassium carbonate (3.2 g, 2.5 eq), 2-(di-tert-butylphosphino)-2',4',6'-triisopropyl-3,6-dimethoxy-1,1'-biphenyl (0.92 g, 0.20 eq), tris(dibenzylideneacetone)dipalladium(0) (0.87 g, 0.10 eq), and acetic acid (0.01 mL) in tert-butyl alcohol (46 mL). Heat at 90° C. overnight. Filter through a pad of diatomaceous earth and wash the pad with EtOAc. Concentrate the filtrate in vacuo to provide a residue. Subject the residue to normal phase chromatography, eluting with 5% MeOH in DCM, to give crude product. Further purify the crude product by reverse phase chromatography, eluting with a 15-60% B in A gradient (A: 10 mM ammonium bicarbonate in MeOH, B: acetonitrile). Concentrate fractions containing product to remove a majority of the acetonitrile. Add EtOAc and separate the layers. Wash the organic layer with saturated aqueous sodium chloride, dry over sodium sulfate, filter and concentrate the filtrate in vacuo. Further purify the product by normal phase chromatography, eluting with a 5% MeOH in DCM, to give the title compound as a white solid (2.4 g, 49%). MS (ES) m/z=525 (M+H).

Example 2

(2R)-1,1,1-Trifluoro-3-({cis-4-[(4-{[1-(2-methoxy-ethyl)-5-methyl-1H-pyrazol-3-yl]amino}-1-methyl-1H-benzimidazol-6-yl)oxy]cyclohexyl}amino)propan-2-ol

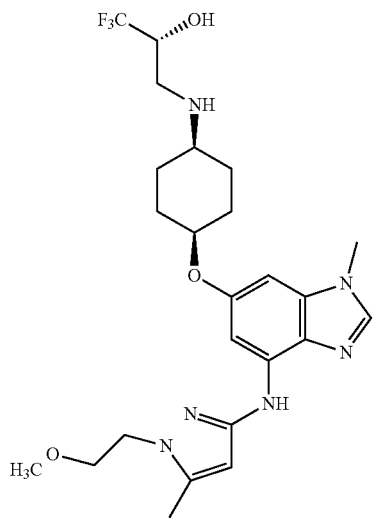

Combine (2R)-3-({cis-4-[(4-bromo-1-methyl-1H-benzimidazol-6-yl)oxy]cyclohexyl}amino)-1,1,1-trifluoropropan-2-ol (1.4 g, 3.2 mmol), 1-(2-methoxyethyl)-5-methyl-1H-pyrazol-3-amine (0.69 g, 1.4 eq), potassium carbonate (1.1 g, 2.6 eq), 2-(dicyclohexylphosphino)3,6-dimethoxy-2',4',6'-triisopropyl-1,1'-biphenyl (0.35 g, 0.20 eq), tris(dibenzylideneacetone)dipalladium(0) (0.15 g, 0.050 eq), and acetic acid (0.01 mL) in tert-butyl alcohol (32 mL). Heat at reflux overnight. Concentrate the reaction mixture in vacuo. Add DCM and water; separate the layers. Filter the organic layer through ISOLUTE® HM-N material, wash with DCM and EtOAc. Concentrate the filtrate in vacuo to provide a residue. Subject the residue to normal phase chromatography, eluting with a 30-100% B in A gradient (A: DCM, B: 15% 2M ammoniated MeOH in DCM), to give the title compound as an off-white solid (0.91 g, 56%). MS (ES) m/z=511 (M+H).

Example 3

(2R)-1,1,1-Trifluoro-3-[(cis-4-{[4-({1-(2-hydroxypropyl)-5-methyl-1H-pyrazol-3-yl}amino)-1-methyl-1H-benzimidazol-6-yl]oxy}cyclohexyl)amino]propan-2-ol

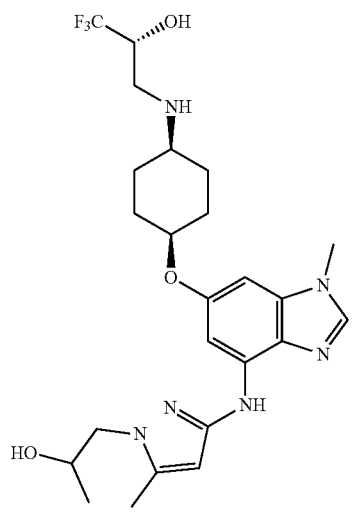 [SMILES: C/C(=C/C(=N)Nc1cc(O[C@H]2CC[C@@H](NC[C@@H](O)C(F)(F)F)CC2)cc2c1ncn2C)NCC(C)O]

Combine (2R)-3-({cis-4-[(4-bromo-1-methyl-1H-benzimidazol-6-yl)oxy]cyclohexyl}amino)-1,1,1-trifluoropropan-2-ol (0.35 g, 0.80 mmol), 1-(3-amino-5-methyl-1H-pyrazol-1-yl)propan-2-ol (0.14 g, 1.1 eq), potassium carbonate (0.28 g, 2.5 eq), 2-(di-tert-butylphosphino)-2',4',6'-triisopropyl-3,6-dimethoxy-1,1'-biphenyl (0.12 g, 0.30 eq), tris(dibenzylideneacetone)dipalladium(0) (0.055 g, 0.075 eq), and acetic acid (0.01 mL) in tert-butyl alcohol (5.3 mL). Heat at 100° C. overnight. Concentrate the reaction mixture in vacuo to provide a residue. Subject the residue to C-18 reverse phase chromatography, eluting with a gradient of 0%-80% of acetonitrile in (10 mM ammonium bicarbonate in methanol). Concentrate fractions containing product (as a mixture of isomers) in vacuo to give the title compound as a white solid (0.29 g, 71%). MS (ES) m/z=511 (M+H).

Separate the isomers in the mixture using the following chiral chromatography conditions to give:

First eluting enantiomer 1 (0.12 g, 99% ee). MS (ES) m/z=511 (M+H), 75%/25% CO$_2$/isopropanol, 5 mL/min, 4.6×150 mm, Chiralpak AD-H Second eluting enantiomer 2 (0.11 g, 97% ee). MS (ES) m/z=511 (M+H), 75%/25% CO$_2$/isopropanol, 5 mL/min, 4.6×150 mm. Chiralpak AD-H

Example 4

(2R)-1,1,1-Trifluoro-3-[(cis-4-{[4-({1-[(2S)-2-hydroxypropyl]-5-methyl-1H-pyrazol-3-yl}amino)-1-methyl-1H-benzimidazol-6-yl]oxy}cyclohexyl)amino]propan-2-ol

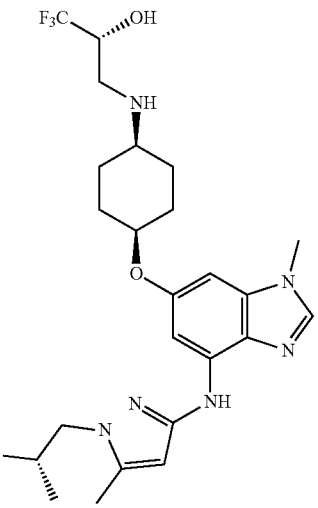

Combine (2R)-3-({cis-4-[(4-bromo-1-methyl-1H-benzimidazol-6-yl)oxy]cyclohexyl}amino)-1,1,1-trifluoropropan-2-ol (0.40 g, 0.92 mmol), (2S)-1-(3-amino-5-methyl-1H-pyrazol-1-yl)propan-2-ol (0.17 g, 1.2 eq), potassium carbonate (0.33 g, 2.6 eq), 2-(dicyclohexylphosphino)3,6-dimethoxy-2',4',6'-triisopropyl-1,1'-biphenyl (0.099 g, 0.20 eq), tris(dibenzylideneacetone)dipalladium(0) (0.042 g, 0.050 eq), and acetic acid (0.01 mL) in tert-butyl alcohol (10 mL). Seal with a crimp cap. Heat the mixture in a microwave reactor at 140° C. for 60 min. Concentrate the reaction mixture in vacuo. Add DCM and water; separate the layers. Filter the organic layer through ISOLUTE® HM-N material, wash the material with DCM and EtOAc. Concentrate the filtrate in vacuo to provide a residue. Triturate the residue with EtOAc/hexanes to give the title compound (0.44 g, 95%). MS (ES) m/z=511 (M+H).

Example 5

(2R)-1,1,1-Trifluoro-3-[(cis-4-{[4-({1-[(2R)-2-hydroxypropyl]-5-methyl-1H-pyrazol-3-yl}amino)-1-methyl-1H-benzimidazol-6-yl]oxy}cyclohexyl)amino]propan-2-ol

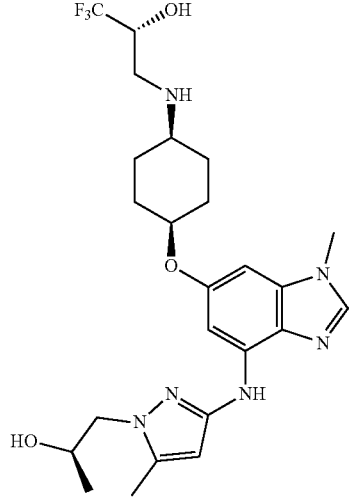 [SMILES: Cc1cc(Nc2cc(O[C@H]3CC[C@@H](NC[C@@H](O)C(F)(F)F)CC3)cc3c2ncn3C)nn1C[C@@H](C)O]

Combine (2R)-3-({cis-4-[(4-bromo-1-methyl-1H-benzimidazol-6-yl)oxy]cyclohexyl}amino)-1,1,1-trifluoropropan-2-ol (0.15 g, 0.34 mmol), (2R)-1-(3-amino-5-methyl-1H-pyrazol-1-yl)propan-2-ol (0.064 g, 1.2 eq), potassium carbonate (0.12 g, 2.6 eq), 2-(dicyclohexylphosphino)3,6-dimethoxy-2',4',6'-triisopropyl-1,1'-biphenyl (0.037 g, 0.20 eq), tris(dibenzylideneacetone)dipalladium(0) (0.016 g, 0.050 eq), and acetic acid (0.01 mL) in tert-butyl alcohol (10 mL). Seal with a crimp cap. Heat the mixture in a microwave reactor at 140° C. for 60 min. Concentrate the mixture in vacuo to provide a residue. Add DCM and water to the residue and separate the layers. Filter the organic layer through ISOLUTE® HM-N material; wash the material with DCM and EtOAc. Concentrate the filtrate in vacuo. Triturate from EtOAc/hexanes to give the title compound as a tan solid (0.11 g, 62%). MS (ES) m/z=511 (M+H).

Example 6

(2R)-1,1,1-Trifluoro-3-{[cis-4-({4-[(5-methoxy-1-methyl-1H-pyrazol-3-yl)amino]-1-methyl-1H-benzimidazol-6-yl}oxy)cyclohexyl]amino}propan-2-ol

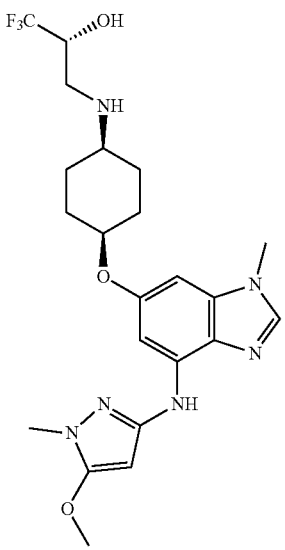 [SMILES: COc1cc(Nc2cc(O[C@H]3CC[C@@H](NC[C@@H](O)C(F)(F)F)CC3)cc3c2ncn3C)nn1C]

Add 2-methylbutan-2-ol (120 mL) to a mixture of (2R)-3-({cis-4-[(4-bromo-1-methyl-1H-benzimidazol-6-yl)oxy]cyclohexyl}amino)-1,1,1-trifluoropropan-2-ol (10 g, 22.9 mmol), 5-methoxy-1-methyl-pyrazol-3-amine (3.6 g, 28.8 mmol), tris(dibenzylideneacetone) dipalladium-(0) (1.8 g, 2 mmol), di-tert-butyl(2',4',6'-triisopropyl-3,6-dimethoxy-[1,1'-biphenyl]-2-yl)phosphine (1.3 g, 2.4 mmol) and potassium carbonate (9 g, 65 mmol). Degas the mixture by bubbling $N_2$ gas through the mixture and then add acetic acid (118 uL, 2 mmol). Heat and stir the mixture under $N_2$ at 100° C. for 20 hr. Cool to rt; evaporate the solvent; then add EtOAc (100 mL), water (50 mL), and charcoal (1 g). Stir the mixture for 15 min and filter the mixture through diatomaceous earth. Collect the filtrate and separate organic layer. Add water (100 mL) and concentrated hydrochloric acid to adjust the pH to 2. Add charcoal (1.5 g), stir the mixture 30 min and filter the mixture through diatomaceous earth. Transfer filtrate to a separator funnel and isolate the aqueous layer. Add concentrated ammonium hydroxide solution over the aqueous layer to adjust the pH to 10 to provide a pale cream solid. Subject the solid to silica gel chromatography eluting with a mixture of methylene chloride and MeOH (95:5). Collect the desired fractions and evaporate the solvent to provide the title compound as pale cream material (6.5 g, 13 mmol) 64% yield.

Crystallize the title compound from cyclopentyl methyl ether (45 mL) to give (2R)-1,1,1-trifluoro-3-[[4-[7-[(5-methoxy-1-methyl-pyrazol-3-yl)amino]-3-methyl-benzimidazol-5-yl]oxycyclohexyl]amino]propan-2-ol (3.2 g, 6.5 mmol). Stir the mixture at 22° C. for 18 h. Evaporate the solvent and dry the white solid to constant weight to afford the title compound as white solid (3.2 g, 6.4 mmol) in 99% yield. MS (m/z): 483.2 (M+H). 1H NMR (300.16 MHz, DMSO): 8.13 (s, 1H), 7.90 (s, 1H), 7.46 (d, J=1.9 Hz, 1H), 6.46 (d, J=1.9 Hz, 1H), 5.49 (s, 1H), 4.45 (s, 1H), 3.83 (s, 3H), 3.73 (s, 3H), 3.47 (s, 3H), 2.75-2.67 (m, 2H), 1.99-1.91 (m, 2H), 1.67-1.54 (m, 7H).

Example 7

(2R)-3-{[(cis-4-({4-[(Ethyl-5-methyl-1H-pyrazol-3-yl)amino]-1-methyl-1H-benzimidazol-6-yl}oxy)cyclohexyl]amino}-1,1,1-trifluoropropan-2-ol

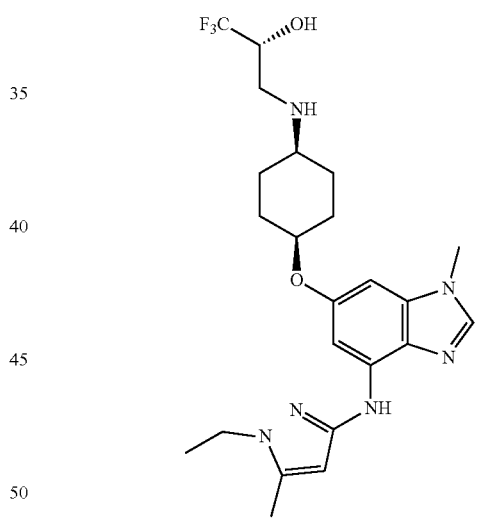

Combine (2R)-3-({cis-4-[(4-bromo-1-methyl-1H-benzimidazol-6-yl)oxy]cyclohexyl}amino)-1,1,1-trifluoropropan-2-ol (1.36 g, 3.12 mmol), 1-ethyl-5-methyl-1H-pyrazol-3-amine (0.78 g, 2.0 eq), potassium carbonate (1.12 g, 2.6 eq), 2-(dicyclohexylphosphino)3,6-dimethoxy-2',4',6'-triisopropyl-1,1'-biphenyl (0.34 g, 0.20 eq), tris(dibenzylideneacetone)dipalladium(0) (0.14 g, 0.050 eq), and acetic acid (0.01 mL) in tert-butyl alcohol (30 mL). Heat at reflux overnight. Concentrate the reaction mixture in vacuo. Add DCM and water; separate the layers. Filter the organic layer through ISOLUTE® HM-N material, washing with DCM. Concentrate the filtrate in vacuo to provide a residue. Triturate the residue in EtOAc and hexanes to give the title compound (1.40 g, 94%). MS (ES) m/z=481 (M+H).

Example 8

(2R)-1,1,1-Trifluoro-3-[(cis-1-methyl-4-{[1-methyl-4-(1H-pyrazol-3-ylamino)-1H-benzimidazol-6-yl]oxy}cyclohexyl)amino]propan-2-ol

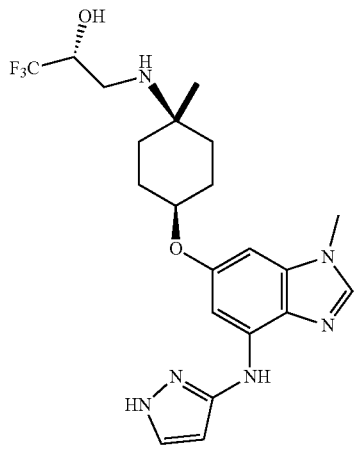 [SMILES: Cn1cnc2c(Nc3cc[nH]n3)cc(O[C@H]3CC[C@@](C)(NC[C@@H](O)C(F)(F)F)CC3)cc21]

Combine (2R)-3-({cis-4-[(4-bromo-1-methyl-1H-benzimidazol-6-yl)oxy]-1-methylcyclohexyl}amino)-1,1,1-trifluoropropan-2-ol (0.91 g, 2.02 mmol), 3-aminopyrazole (0.29 g, 1.70 eq), potassium carbonate (0.73 g, 2.6 eq), 2-(dicyclohexylphosphino)3,6-dimethoxy-2',4',6'-triisopropyl-1,1'-biphenyl (0.22 g, 0.20 eq), tris(dibenzylideneacetone)dipalladium(0) (0.093 g, 0.050 eq), and acetic acid (0.01 mL) in tert-butyl alcohol (20 mL). Reflux the mixture overnight. Concentrate the mixture in vacuo. Add DCM and water; separate the layers. Filter the organic layer through ISOLUTE® HM-N material, washing with DCM. Concentrate the filtrate in vacuo to provide a residue. Subject the residue to normal phase chromatography, eluting with a 50-100% B in A gradient (A: methyl tert-butyl ether, B: 15% 7M ammoniated MeOH in DCM), to give the title compound (0.67 g, 74%). MS (ES) m/z=453 (M+H).

Example 9

(2R)-3-{[cis-4-({4-[(1,5-Dimethyl-1H-pyrazol-3-yl)amino]-1-methyl-1H-benzimidazol-6-yl}oxy)cyclohexyl]amino}-1,1-difluoropropan-2-ol

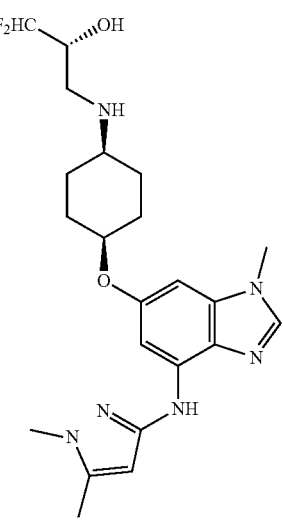

Combine (2R)-3,3-difluoro-2-hydroxypropyl 4-methylbenzenesulfonate (0.38 g, 1.31 mmol) and 6-[(cis-4-aminocyclohexyl)oxy]-N-(1,5-dimethyl-1H-pyrazol-3-yl)-1-methyl-1H-benzimidazol-4-amine (0.61 g, 1.30 eq) in acetonitrile (3 mL) and 2-propanol (3 mL). Add N,N-diisopropylethylamine (0.50 mL, 2.0 eq) and sodium iodide (0.015 g, 0.1 eq). Heat at 65° C. overnight. Add (2R)-3,3-difluoro-2-hydroxypropyl 4-methylbenzenesulfonate (0.065 g, 0.22 mmol) and heat at 65° C. overnight. Filter through diatomaceous earth. Wash the solids with EtOAc. Concentrate the filtrate in vacuo. Purify by reverse phase chromatography, eluting with a 0-90% acetonitrile in water gradient. Concentrate fractions containing product in vacuo to give the title compound as an off-white solid (0.40 g, 67%). MS (ES) m z=449 (M+H).

Example 10

(2R)-1,1,1-Trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol

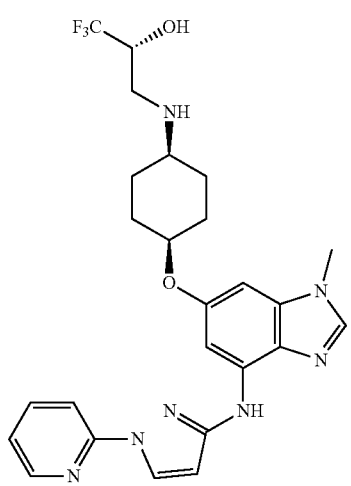 [SMILES: Cn1cnc2c(NC(=N)/C=C\Nc3ccccn3)cc(O[C@H]3CC[C@@H](NC[C@@H](O)C(F)(F)F)CC3)cc21]

Combine (2R)-3-({cis-4-[(4-bromo-1-methyl-1H-benzimidazol-6-yl)oxy]cyclohexyl}amino)-1,1,1-trifluoropropan-2-ol (1.8 g, 4.1 mmol), 1-pyridin-2-yl-1H-pyrazol-3-amine (0.86 g, 1.3 eq), potassium carbonate (1.7 g, 2.9 eq), 2-(di-tert-butylphosphino)-2'4',6'-triisopropyl-3,6-dimethoxy-1,1'-biphenyl (0.83 g, 0.41 eq), tris(dibenzylideneacetone)dipalladium(0) (0.38 g, 0.10 eq), and acetic acid (0.03 mL) in tert-butyl alcohol (22 mL). Heat the mixture at 90° C. for three hours. Cool the mixture to rt. Filter through a pad of diatomaceous earth and wash the pad with EtOAc. Concentrate the filtrate in vacuo to provide a residue. Subject the residue to normal phase chromatography, eluting with a 0-10% MeOH in DCM gradient, to give the title compound (1.34 g, 63° %.). MS (ES) m/z=516 (M+H).

Crystalline free base material can be obtained by dissolving the solid material, which is prepared substantially as described above, in 2 butanone (100 mass %) then heating the resulting mixture to 65° C. Allow the mixture to cool to 20° C., and add heptane (100 mass %) to induce participation. Collect the resulting solid and wash with heptane, air dry for 15 minutes, then dry in the oven at 40° C. overnight to provide the title compound as an anhydrous crystalline free base in 62% yield.

X-Ray Powder Diffraction of Example 10

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 38—National Formulary 35 Chapter Characterization of crystalline and partially crystalline solids by X-ray powder diffraction (XRPD) Official May 1, 2015. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2-theta.

Thus, a prepared sample of the free base compound of Example 10 is characterized by an XRD pattern using CuKa radiation as having diffraction peaks (2-theta values) as described in Table 1 below. Specifically the pattern contains a peak at 20.5 in combination with one or more of the peaks selected from the group consisting of 15.5, 18.1, 18.3, 18.5, 22.9 and 23.6 with a tolerance for the diffraction angles of 0.2 degrees.

TABLE 1

| X-ray powder diffraction peaks of Example 10 | | |
|---|---|---|
| Peak | Angle 2theta | % Intensity |
| 1 | 11.3 | 21% |
| 2 | 13.2 | 37% |
| 3 | 14.8 | 22% |
| 4 | 15.5 | 63% |
| 5 | 16.3 | 19% |
| 6 | 18.1 | 63% |
| 7 | 18.3 | 75% |
| 8 | 18.5 | 56% |
| 9 | 19.0 | 30% |
| 10 | 19.3 | 27% |
| 11 | 20.5 | 100% |
| 12 | 20.8 | 19% |
| 13 | 22.3 | 16% |
| 14 | 22.9 | 86% |
| 15 | 23.3 | 30% |
| 16 | 23.6 | 49% |
| 17 | 23.7 | 45% |
| 18 | 24.7 | 36% |
| 19 | 25.5 | 28% |
| 20 | 26.5 | 33% |

TABLE 1-continued

| X-ray powder diffraction peaks of Example 10 | | |
|---|---|---|
| Peak | Angle 2theta | % Intensity |
| 21 | 28.3 | 19% |
| 22 | 31.0 | 17% |

Examples 11A and 11B (2R)-1,1,1-Trifluoro-3-[(cis-4-{[1-methyl-4-({1-[(3R)-tetrahydro-2H-pyran-3-yl]-1H-pyrazol-3-yl}amino)-1H-benzimidazol-6-yl]oxy}cyclohexyl)amino]propan-2-ol

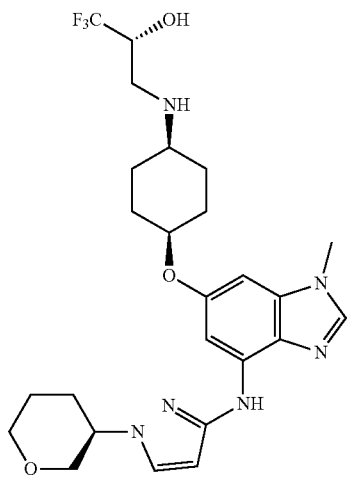 [SMILES: Cn1cnc2c(NC(=N)/C=C\N[C@@H]3CCCOC3)cc(O[C@H]3CC[C@@H](NC[C@@H](O)C(F)(F)F)CC3)cc21]

(2R)-1,1,1-Trifluoro-3-[(cis-4-{[1-methyl-4-({1-[(3S)-tetrahydro-2H-pyran-3-yl]-1H-pyrazol-3-yl})amino)-1H-benzimidazol-6-yl]oxy}cyclohexyl)amino]propan-2-ol

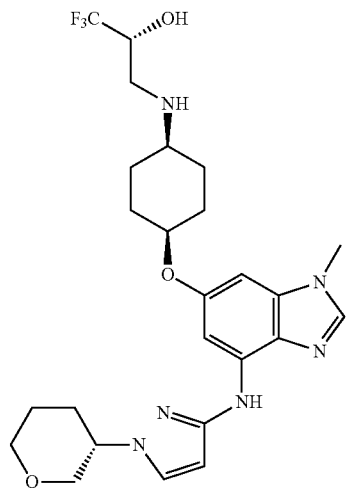 [SMILES: Cn1cnc2c(NC(=N)/C=C\N[C@H]3CCCOC3)cc(O[C@H]3CC[C@@H](NC[C@@H](O)C(F)(F)F)CC3)cc21]

First prepare the compounds as a racemic mixture. Combine (2R)-3-({cis-4-[(4-bromo-1-methyl-1H-benzimidazol-6-yl)oxy]cyclohexyl}amino)-1,1,1-trifluoropropan-2-ol (0.62 g, 1.2 eq), 1-(tetrahydro-2H-pyran-3-yl)-1H-pyrazol-3-amine (0.20 g, 1.2 mmol), potassium carbonate (0.42 g, 2.5 eq), 2-(di-tert-butylphosphino)-2',4',6'-triisopropyl-3,6-dimethoxy-1,1'-biphenyl (0.18 g, 0.30 eq), tris(dibenzylideneacetone)dipalladium(0) (0.085 g, 0.075 eq), and acetic acid (0.02 mL) in tert-butyl alcohol (6 mL). Heat at 100° C.

for seven hrs. Allow the reaction mixture to cool to rt. Concentrate the reaction mixture in vacuo. Dilute with EtOAc. Filter through a pad of diatomaceous earth and wash the pad with EtOAc. Add saturated aqueous sodium bicarbonate to the filtrate. Separate the layers. Wash the organic layer with water and brine. Dry the organic layer over anhydrous MgSO$_4$, filter, and concentrate the filtrate in vacuo to provide a residue. Subject the residue to normal phase chromatography, eluting with a 0-30% MeOH in DCM gradient, to give the title compound (0.31 g, 49%). MS (ES) m/z=523 (M+H).

Separate the isomers by first preparing the 5-(trifluoromethyl)oxazolidin-2-one derivative:

(5R)-3-(cis-4-{[1-Methyl-4-({1-[(3R)-tetrahydro-2H-pyran-3-yl]-1H-pyrazol-3-yl}amino)-1H-benzimidazol-6-yl]oxy}cyclohexyl)-5-(trifluoromethyl)-1,3-oxazolidin-2-one

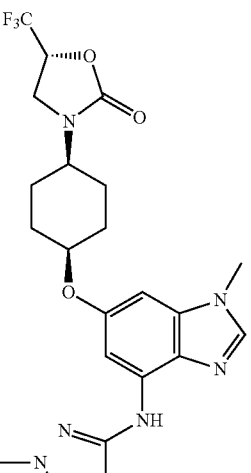

and (5R)-3-(cis-4-{[1-Methyl-4-({1-[(3S)-tetrahydro-2H-pyran-3-yl]-1H-pyrazol-3-yl}amino)-1H-benzimidazol-6-yl]oxy}cyclohexyl)-5-(trifluoromethyl)-1,3-oxazolidin-2-one

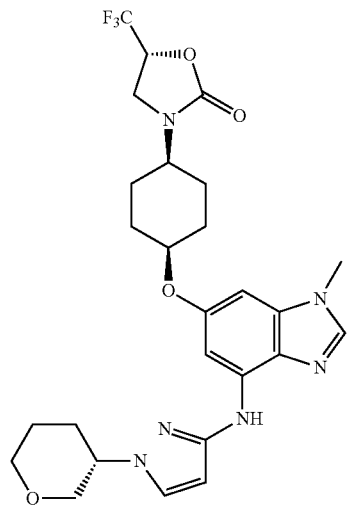 [SMILES: Cn1cnc2c(NC(=N)/C=C\N[C@H]3CCCOC3)cc(O[C@H]3CC[C@@H](N4C[C@H](C(F)(F)F)OC4=O)CC3)cc21]

Combine (2R)-1,1,1-trifluoro-3-({cis-4-[(1-methyl-4-{[1-(tetrahydro-2H-pyran-3-yl)-1H-pyrazol-3-yl]amino}-1H-benzimidazol-6-yl)oxy]cyclohexyl}amino)propan-2-ol (0.25 g, 0.42 mmol), 1,1'-carbonyldiimidazole (0.14 g, 2.0 eq), and 4-dimethylaminopyridine (0.011 g, 0.21 eq) in DCM (2 mL). Stir at rt for three days. Concentrate in vacuo to provide a residue. Subject the residue to normal phase chromatography, eluting with a 0-20% MeOH in DCM gradient, to give racemic mixture of (5R)-3-(cis-4-{[1-methyl-4-({1-[tetrahydro-2H-pyran-3-yl]-1H-pyrazol-3-yl}amino)-1H-benzimidazol-6-yl]oxy}cyclohexyl)-5-(trifluoromethyl)-1,3-oxazolidin-2-one. Separate isomers by chiral chromatography using 60%/40% CO$_2$/isopropanol, 5 mL/min, 4.6×150 mm, Lux Amylose-2.

Isomer 1 (0.10 g, 99% ee). Retention time 2.98 min. MS (ES) m/z=549 (M+H)

Isomer 2 (0.10 g, 99% ee). Retention time 4.83 min. MS (ES) m/z=549 (M+H)

Isomer 1

(2R)-1,1,1-Trifluoro-3-({cis-4-[(1-methyl-4-{[1-(tetrahydro-2H-pyran-3-yl)-1H-pyrazol-3-yl]amino}-1H-benzimidazol-6-yl)oxy]cyclohexyl}amino)propan-2-ol Combine (5R)-3-(cis-4-{[1-methyl-4-({1-[tetrahydro-2H-pyran-3-yl]-1H-pyrazol-3-yl}amino)-1H-benzimidazol-6-yl]oxy}cyclohexyl)-5-(trifluoromethyl)-1,3-oxazolidin-2-one (Isomer 1) (0.080 g, 0.15 mmol) and potassium trimethylsilanolate (0.041 g, 2.0 eq) in THF (2 mL). Stir at 65° C. for three days. Add potassium trimethylsilanolate (0.018 g, 1.0 eq). Stir at 65° C. overnight. Allow to cool to rt. Dilute with a few drops of water and concentrate in vacuo. Purify by C-18 reverse phase chromatography using 0%-100% acetonitrile in (10 mM ammonium bicarbonate in methanol) gradient, to give the title compound (0.055 g, 72%). MS (ES) m/z=523 (M+H).

Isomer 2

(2R)-1,1,1-Trifluoro-3-({cis-4-[(1-methyl-4-{[1-(tetrahydro-2H-pyran-3-yl)-1H-pyrazol-3-yl]amino}-1H-benzimidazol-6-yl)oxy]cyclohexyl}amino)propan-2-ol Combine (5R)-3-(cis-4-{[1-methyl-4-({1-[tetrahydro-2H-pyran-3-yl]-1H-pyrazol-3-yl}amino)-1H-benzimidazol-6-yl]oxy}cyclohexyl)-5-(trifluoromethyl)-1,3-oxazolidin-2-one (Isomer 2) (0.080 g, 0.15 mmol) and potassium trimethylsilanolate (0.040 g, 2.0 eq) in THF (2 mL). Stir at 65° C. for three days. Add potassium trimethylsilanolate (0.018 g, 1.0 eq). Stir at 65° C. overnight. Allow to cool to rt. Dilute with a few drops of water and concentrate in vacuo. Purify by C-18 reverse phase chromatography using a 0%-100% acetonitrile in (10 mM ammonium bicarbonate in methanol) gradient, to give the title compound (0.058 g, 76%). MS (ES) m/z=523 (M+H).

Example 12

(2R)-1,1,1-Trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate Hydrate (1:1:1)

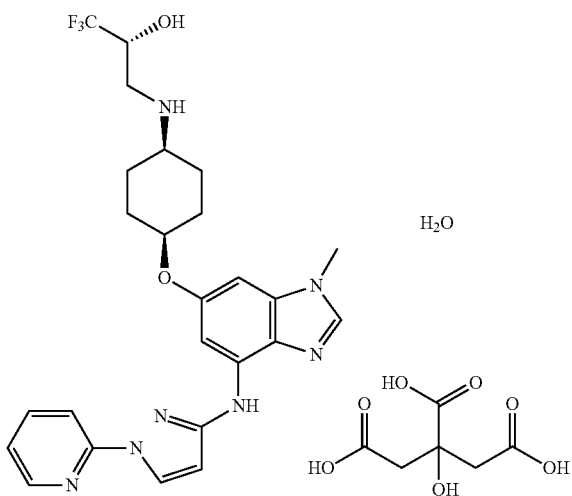 [SMILES: Cn1cnc2c(NC(=N)/C=C\Nc3ccccn3)cc(O[C@H]3CC[C@@H](NC[C@@H](O)C(F)(F)F)CC3)cc21 ; O=C(O)CC(O)(CC(=O)O)C(=O)O ; O]

Add 1.23 g of (2R)-1,1,1-Trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol to 10 mL of 88% acetone while stirring at 1000 rpm/70° C., to obtain a white slurry. Add 510 mg of citric acid dropwise. The white slurry turns to a clear yellowish solution. Discontinue heating and stirring. Over the next hour, a yellow solid slowly forms. Isolate the light yellow solid by vacuum filtration. Dry the sample on the filter under air stream for 20 minutes to yield the title compound. (1.62 g, 93.6%)

X-Ray Powder Diffraction of Example 12:

The XRD patterns of crystalline solids are obtained on a Bruker D4 Endeavor X-ray powder diffractometer, equipped with a CuKa source (λ=1.54060 Å) and a Vantec detector, operating at 35 kV and 50 mA. The sample is scanned between 4 and 40° in 2θ, with a step size of 0.0087° in 2θ and a scan rate of 0.5 seconds/step, and with 0.6 mm divergence, 5.28 mm fixed anti-scatter, and 9.5 mm detector slits. The dry powder is packed on a quartz sample holder and a smooth surface is obtained using a glass slide. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The U. S. Pharmacopeia 38—National Formulary 35 Chapter Characterization of crystalline and partially crystalline solids by X-ray powder diffraction (XRPD) Official May 1, 2015. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of +0.2 in 2θ will take into account these potential variations without hindering the unequivocal identification of the indicated crystal form. Confirmation of a crystal form may be made based on any unique combination of distinguishing peaks (in units of ° 2θ), typically the more prominent peaks. The crystal form diffraction patterns, collected at ambient temperature and relative humidity, are adjusted based on NIST 675 standard peaks at 8.85 and 26.77 degrees 2-theta.

An XRD pattern of (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate (1:1:1) using CuKa radiation provides diffraction peaks (2-theta values) as described in Table 2 below, and in particular having peaks at 17.9 in combination with one or more of the peaks selected from the group consisting of 26.1, 26.6, and 22.7; with a tolerance for the diffraction angles of 0.2 degrees.

TABLE 2

X-ray powder diffraction peaks of the crystalline (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate (1:1:1)

| Peak | Angle (°2-Theta) +/− 0.2° | Relative Intensity (% of most intense peak) |
|---|---|---|
| 1 | 4.7 | 8% |
| 2 | 9.5 | 40% |
| 3 | 10.0 | 30% |
| 4 | 11.2 | 29% |
| 5 | 17.2 | 45% |
| 6 | 17.9 | 100% |
| 7 | 18.7 | 36% |
| 8 | 22.7 | 52% |
| 9 | 26.1 | 100% |
| 10 | 26.6 | 63% |

Biological Section
JAK1, JAK2 and JAK3 In Vitro Enzyme Assays

The JAK LanthaScreen™ Kinase Assay (Invitrogen) is used to determine the ability of test compounds to inhibit JAK1, JAK2, and JAK3 kinase activity. These are TR-FRET assay formats that use long-lifetime terbium labeled antibody as the donor species and GFP-STAT1 as the acceptor species. Use the TR-FRET ratio to monitor JAK kinase activity where an increase in phosphorylation of the GFP-STAT1 results in an increase in the TR-FRET ratio. Perform the kinase reaction using a 12.5 µl reaction volume in shallow black 384-well Proxiplate®. Add reagents to obtain final reaction conditions of 50 ml HEPES pH, 1.76 mM Triton X-100, ATP (20.0 µM for JAK1 and JAK3 or 5 µM for JAK2) enzyme assays, 10.0 mM MgCl₂, 1 mM EGTA and 0.01% Brij-35, 0.05 mM GFP-STAT1, 14 nM JAK1 enzyme for JAK1, 1.0 nM for JAK2 or 2.5 nM for JAK3 enzyme assays, and 4% DMSO and serial dilutions of test compound (diluted 1:3 from 20,000 to 1 nM). Following ATP/GFP-STAT1 addition, centrifuge the assay plates for 1 minute at 1000 revolutions per minute (RPM). Allow the plates to incubate at RT for 60 minutes and then add 12.5 µl of a stopping buffer containing 20 mM EDTA, 2 nM Terbium-anti-phosphorylated Signal Transducers and Activators of Transcription [phosphorylation Tyrosine 701 amino acid] Antibody (Tb-anti-pSTAT1 [pTyr701], 0.67 mM tris(hydroxymethyl)aminoethane hydrochloride (Trizma®) pH 7.5, 0.02% NaN₃ and 0.01% nonylphenylpolyethylene glycol (Nonidet® P40). Incubate at RT 90 min and read in an EnVision® plate reader with 340 nm wavelength excitation filter and emission filters of 520 nm and 495 nm wavelengths. Derive the ratio from the emission wavelength for the GFP-STAT1 which is measured at 520 nm versus the emission at 495 nm for the (Tb-anti-pSTAT1 [pTyr701]. Derive the $IC_{50}$ value for each compound using percent inhibition data which is calculated from the reaction data relative to on-plate controls (active enzyme versus enzyme inhibited at 2.0 mM with tofacitinib). Use ACTIVI-TYBASE® 4.0 to fit the percent inhibition and ten-point compound concentration data to a four-parameter logistic equation.

Following a protocol essentially as described above, the compounds of the Examples herein were tested. The compounds of the Examples exhibited a $IC_{50}$ for JAK1 of less than 8 nM and are selective inhibitors of JAK1 over JAK2, or JAK3 in vitro. The compounds of Examples 1 and 6 to 10 exhibited the activity listed in Table 3.

TABLE 3

| Example No. | JAK1 $IC_{50}$ (nM) | JAK2 $IC_{50}$ (nM) | JAK3 $IC_{50}$ (nM) |
| --- | --- | --- | --- |
| 1 | 3.25 ± 0.99 (n = 3) | 1200 ± 550 (n = 3) | 3720 ± 1300 (n = 3) |
| 6 | 5.25 ± 1.11 (n = 5) | 768 ± 220 (n = 5) | 2540 ± 510 (n = 5) |
| 7 | 5.43 ± 0.93 (n = 3) | 901 ± 99 (n = 3) | 6160 ± 2020 (n = 3) |
| 8 | 1.91 ± 0.75 (n = 4) | 239 ± 150 (n = 4) | 1170 ± 470 (n = 4) |
| 9 | 5.35 ± 0.23 (n = 5) | 767 ± 39 (n = 5) | 2140 ± 720 (n = 5) |
| 10 | 1.49 ± 0.49 (n = 3) | 220 ± 120 (n = 3) | 660 ± 180 (n = 3) |

The data demonstrate that the compounds of the Examples are inhibitors of JAK1 enzyme and selective to JAK1 over JAK2 and JAK3 in vitro.

AlphaScreen SureFire Protocol p-STAT3-(p-Tyr705)-IL6-TF-1-JAK1 Cell-Based Assay

The JAK1 cell based assay described below is used to determine the JAK1 cellular potency of test compounds.

Cell preparation: Starve TF-1 cells in DMEM medium with 0.5% 26400 (FBS) and 1× Pen/Strep at 37° C. Plate 100K cells per well in BD 96 well black plates with clear bottoms. Maintain the plates at RT for 30-60 minutes before incubating overnight at 37° C., and 5% $CO_2$. Count cells using Vi-Cell counter, using a cell suspension at 100 cells/mL and plated 100 µL/well in Beckman Dickinson Biocoat plates (Catalog #354640).

Test compound preparation and treatment: Prepare compounds at 1:3 serial dilutions in DMSO and further dilute into the medium. Test compounds in a range of 10 point concentrations from 20,000 to 1 nM. Add diluted compound to corresponding cell plates. Incubate the plates at 37° C. for 20 min. Add IL6 solution at the final concentration 30 ng/mL to corresponding cell plates and continue to incubate at 37° C. for 30 min. Remove media and add 50 µL 1× lysis buffer to each well.

pSTAT3 detection: Perform the following steps sequentially: make acceptor mix (activation buffer/reaction buffer/acceptor beads); transfer 4 µL lysate from 96 well plates to 384 well-Proxiplates; add 5 µL acceptor mix to 384 proxiplate plate(s) and seal plates with aluminum seal; shake 1-2 minutes on plate shaker; incubate plate at RT for 2 hr with gentle shaking; make donor mix (donor beads in dilution buffer); add 2 µL donor mix to assay plates; seal plates with aluminum seal; shake 1-2 minutes on plate shaker; incubate at RT for 2 hr with gentle shaking; read plate with Envision; protocol AlphaScreen Surefire 384.

Following a protocol essentially as described above, the compounds of Examples 1, 2, and 6 were tested and exhibited the following activity as illustrated in Table 4 below.

TABLE 4

| Example No. | $IC_{50}$(nM) |
| --- | --- |
| 1 | 0.154 ± 0.023 (n = 2) |
| 2 | 0.275 ± 0.102 (n = 3) |
| 6 | 0.168 ± 0.090 (n = 4) |

The data in Table 4 demonstrate that the compounds of Examples 1, 2, and 6 inhibit the JAK1 enzyme in a cell based assay provides support that the compounds of the Examples also inhibit the JAK1 enzyme in the cell.

Human Whole Blood Assays: Determination of pSTAT3 (JAK1) and pSTAT5 (JAK2) in Lymphocytes and Monocytes Human whole blood (HWB) assays were developed and validated to determine the JAK1 and JAK2 selectivity of test compounds.

Dilute the test compounds, 10 points, (1:3) in DMSO 100% and a step down in PBS+0.1% BSA. Use Tofacitinib as a reference compound in each plate, as well as a maximum signal (stimulated wells) and a minimum signal (no stimulated wells) in order to normalize data. Obtain a pool of HWB from 4 different healthy donors. Plate the blood in a 96 well plate using a Tecan Evo 96w and incubate with test compounds for 1 h at RT. After this time of incubation, stimulate HWB with both IL6 (206-IL, R&D System) and GM-CSF (PHC2015, Life Technologies) for 15 more minutes. Add a viability dye (65-0865, eBiosicience) (1:1000) using a Tecan Evo 96w (5×mix).

The final concentrations in the assay are the following: 100 (µM for compounds, 50 µM for Tofacitinib, 0.1 µg/mL IL6, 0.038 µg/mL GM-CSF and 1% DMSO. Lyse and fix HWB using a Lyse/fix buffer (558049, Becton Dickinson) by adding 900 µL of lysis buffer using Tecan Evo 96w (mix 10× high speed). Incubate HWB in bath at 37° C. for 10 minutes. Centrifuge HWB at 500 G, 8 min and discard supernatant. Add cold MeOH using a Tecan Exo 96w in order to permeabilize cells. Incubate blood cells on ice during 30 min. After this, wash cells 2× using Staining buffer (554656, Becton Dickinson), spin at 3000 rpm, 2 min. discard supernatant, and add the following antibodies: Anti-Human CD4 PE, 1:100 (12-0048, eBioscience), Anti-Human CD33 eFluor® 450, 1:50 (48-0337, eBioscience), Phospho-STAT5 (Tyr694) (C71E5) Rabbit mAb, 1:100 (Alexa Fluor® 488 Conjugate) (3939, Cell Signaling) and Phospho-STAT3 (Tyr705) (D3A7) XP™ Rabbit mAb 1:200, (Alexa Fluor® 647 Conjugate) (4324, Cell Signaling). Incubate the antibodies for 1 h in dark at RT, then wash cells 2× and read on Cytometer Macsquant (Miltenyi Biotec). Gate the data on CD4+ (lymphocytes) and CD4Low CD33Hi (monocytes), to measure the fluorescence intensity from cells expressing pSTAT3 and pSTAT5, respectively. Analyze the data using FlowJo v 10 and then normalize the median of fluorescence versus maximum and minimum signal to determine the $IC_{50}$s. Use Graph Pad Prism 5™ to represent the dose response curves.

Following a protocol essentially as described above, the compounds of the Examples herein were tested. The compounds of the Examples exhibited greater selectivity for JAK1 over JAK 2. The activity for the compounds of Examples 6 to 10 are listed in Table 5.

TABLE 5

| Example No. | JAK1 IC$_{50}$(µM) | JAK2 IC$_{50}$(µM) |
|---|---|---|
| 6 | 3.65 ± 0.79 (n = 7) | 20.3 ± 6.3 (n = 6) |
| 7 | 4.17 ± 1.87 (n = 6) | 18.6 ± 6.1 (n = 5) |
| 8 | 3.13 ± 1.1 (n = 6) | 9.63 ± 2.52 (n = 6) |
| 9 | 4.53 ± 2.09 (n = 7) | 16.9 ± 4.5 (n = 6) |
| 10 | 1.29 ± 0.64 (n = 3) | 6.86 ± 2.13 (n = 3) |

The data in Table 5 demonstrate that the compounds of the Examples are more potent for JAK1 over JAK2 in a human whole blood assay.

Rat PK/PD Assay

Male Wistar rats, 265-285 grams (Charles River) were used for oral gavage dosing. Dose the animals (Oral gavage) at 1.82 mL/kg (0.5 mL per 275 grams). Formulate the compounds in 1% HEC vehicle containing 0.25% Tween 80 and 0.05% antifoam with 1.1 molar equivalent of methanesulfonic acid to form an in situ salt. Formulate compounds once per week, and store at 4° C. At various time points, obtain rat whole blood via tail vain bleeding in Multivette 600 µl EDTA blood collection tubes (cat#151671100PK100, Sarstedt Inc) and use for ex vivo JAK1 and JAK2 assay. Aliquot 100 ul of blood from each rat into a 96-well round bottom plate. Stimulate whole blood by recombinant IL-6 (00 ng/ml, and recombinant mouse GM-CSF (cat#415-ML, lot#, R&D) for 12 min at rt. After cytokine stimulation, add whole blood into Lyse/fix (cat#558049, lot#, BD) in minitube rack; mix well 5×. Incubate 10 min at rt. Spin minitube rack at 600 g for 4 min. Aspirate with 12-channel manifold. Transfer contents of minitube rack to 96 well round-bottom plates. Spin down the cells at 3000 rpm for 1 min and discard the supernatant. Mix the cells in the well with 100 ul ice-cold MeOH and incubated on ice for 30 min. Add 150 ul PBS+2% FCS into each well and spin down at 3000 rpm, 2 min. Wash cells with 2× of 250 ul PBS+2% FCS. For cell surface and intracellular staining, mix all antibodies and add into each well and incubate 1 hr at rt in dark. The antibodies used for staining are as following: pSTAT3, Alexa Fluor 647 (cat#4324s, lot, Cell Signaling); pSTAT5, Alexa Fluor 488 (cat#3939s, lot#, Cell Signaling), anti-rat CD4, V450 (cat#561579, lot#. BD); anti-rat CD11b, Percp eFluor710 (cat#12-0110-82, lot#, eBioscience) After staining cells with Abs, wash the plates twice with PBS+2% FCS and finally re-suspend in the same 150 ul of solution. Assess cell viability by Viability Dye 780 (cat#65-0865-14, lot#, eBioscience). Perform the cytometry assay using FORTESSA.

Following a protocol essentially as described above, the compounds of Examples 4, and 6 to 10 and were tested, and the data is listed in Table 6.

TABLE 6

Rat whole blood ex vivo JAK1 and JAK2 activity (% inhibition at 30 mpk compared with vehicle treatment as 100% inhibition)

| Example No. | JAK1 inhibition 2 hr post dosing (%) | JAK2 inhibition 2 hr post dosing (%) | JAK1 inhibition 7 hr post dosing (%) | JAK2 inhibition 7 hr post dosing (%) |
|---|---|---|---|---|
| 4 | 72.0 | 22.9 | 22.3 | 20.1 |
| 6 | 83.5 | 17.7 | 75.4 | 17.4 |
| 7 | 70.7 | 10.7 | 61.0 | 3.40 |

This data support the activity of the compounds of the Examples and that they are more potent for JAK1 over JAK2 in rats in vivo.

Rat Collagen-Induced Arthritis (CIA) Model

This protocol uses Lewis rats (weight 150-175 grams) from Charles River. On day 0, anesthetize rats with Isoflurane. On day 1, immunize intradermally with collagen emulsion in two sites on the lower lumbar region, above the base of the tail. Dose volume is a minimum of 0.4 mL per injection site. On day 8, anesthetize rats with Isoflurane and immunize intradermally with collagen emulsion in two sites on the lower lumbar region, above the base of the tail. Enroll rats into treatment groups on day 12, based on inflammation (redness and/or swelling) in their hind paws. Randomize animals for Treatment Phase based on ankle measurement values and body weight using block randomization allocation tool. Record ankle swelling on days 1, 8, and 11 and then three times per week following enrollment up to and including the day of necropsy. Dose compounds orally once a day starting on day 12 (after randomization) up to day 25. The compounds of Examples 6 and 7 were evaluated in the protocol essentially as described above. The results are listed in Table 7 below.

TABLE 7

Rat paw swelling inhibition (% inhibition compared with naive rat as 100% inhibition)

| Example No. | % inhibition at 30 mpk | % inhibition at 10 mpk | % inhibition at 3 mpk |
|---|---|---|---|
| 6 | 79 | 47 | 12 |
| 7 | 73 | 69 | 0 |

The data in Table 7 demonstrate that the compounds of Examples 6 and 7 exhibit a dose responsive inhibition of paw swelling in rats, and lend support that the compounds of the Examples can be efficacious in the treatment of arthritis.

Rat Adjuvant-Induced Arthritis (AIA) Model

The effects of compounds on polyarthritis inflammation and ankle joint bone erosion can be evaluated in a rat adjuvant-induced arthritis (AIA) model. Use Male Lewis rats with a mean body weight of 185 g for the study. Induce arthritis by intra-dermal injection located at the base of the tail with 100 µL of adjuvant suspended immunization emulsion oil. Randomize animals based on the mean paw thickness and body weight on day 10 into study groups with 8 rats in each group. Prepare compounds in 1% HEC/0.25% P80/0.05% AF in purified water and dose daily via oral gavage starting from day 11 post immunization for 14 days. Quantitate paw thickness with the caliper measurement on both ankles. Assess group differences using a one-way ANOVA followed by Dunnett's post-test for multiple comparisons against vehicle controls. The compound of Example 10 are evaluated in the protocol essentially as described above. The results are listed in Table 8 below.

TABLE 8

Paw swelling and bone mineral density (BMD) loss inhibition (% inhibition compared, with naïve rat as 100% inhibition) in rat AIA model

| Example No. 10 dose | % inhibition of paw swelling | % inhibition of BMD loss in paw |
|---|---|---|
| 3 mpk | 26 | 39 |
| 10 mpk | 63 | 81 |
| 30 mpk | 73 | 84 |

The data in Table 8 demonstrate that the compound of Example 10 exhibit a dose responsive inhibition of paw swelling in rats, and lend support that the compound of the Example can be efficacious in the treatment of arthritis.

What is claimed is:

1. A compound of the formula, or a pharmaceutically acceptable salt thereof

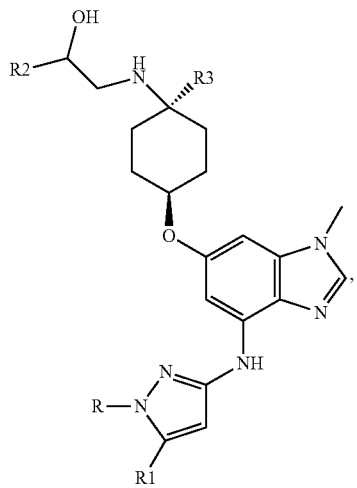

wherein R is selected from:

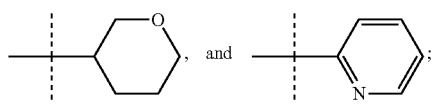

R1 is selected from: H or —CH₃;
R2 is —CHF₂ or —CF₃; and
R3 is H or —CH₃.

2. A compound according to claim 1 of the formula, or a pharmaceutically acceptable salt thereof,

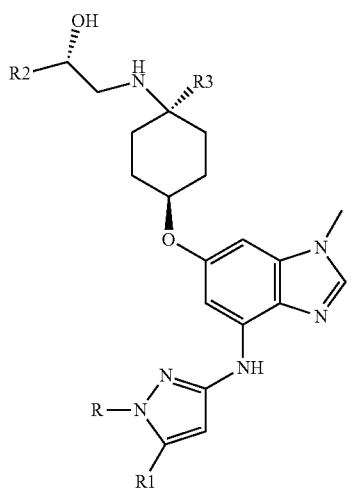

wherein:
R is selected from:

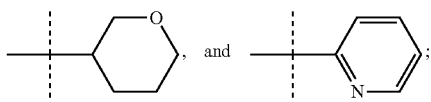

R1 is selected from: H or —CH₃;
R2 is —CHF₂ or —CF₃; and
R3 is H or —CH₃.

3. A compound according to claim 2 wherein R is

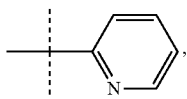

or a pharmaceutically acceptable salt thereof.

4. A compound according to claim 3 wherein R2 is —CF₃, or a pharmaceutically acceptable salt thereof.

5. A compound according to claim 1 which is

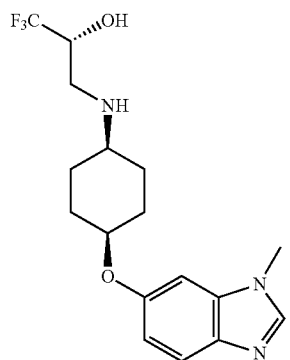

or a pharmaceutically acceptable salt thereof.

6. A compound according to claim 1 which is

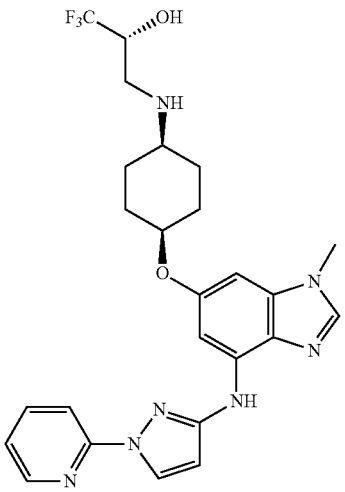 [SMILES: Cn1cnc2c(Nc3ccn(-c4ccccn4)n3)cc(O[C@H]3CC[C@@H](NC[C@@H](O)C(F)(F)F)CC3)cc21]

or a pharmaceutically acceptable salt thereof.

7. A compound which is (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate.

8. A compound according to claim 6 which is (2R)-1,1,1-Trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol in crystalline form characterized by an X-ray powder diffraction pattern obtained from a CuKα source (λ=1.54056 Å), which comprises peaks at:
a) 15.5, 18.1, 18.3, 20.5, and 22.9+/−0.2° in 2 theta, or
b) 13.2, 15.5, 18.1, 18.3, 18.5, 20.5, 22.9, and 23.6, 23.7, +/−0.2° in 2 theta, or
c) 13.2, 15.5, 18.1, 18.3, 18.5, 19.0, 20.5, 22.9, 23.6, 23.6, 23.7, 24.7, and 26.5+/−0.2° in 2 theta.

9. A compound according to claim 7 which is (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate in crystalline foam characterized by an X-ray powder diffraction pattern obtained from a CuKα source (λ=1.54060 Å), having a peak at 17.9 in combination with one or more of the peaks selected from the group consisting of 26.1, 26.6, and 22.7, with a tolerance for the diffraction angles of 0.2 degrees.

10. A pharmaceutical composition comprising a compound according to claim 1 and a pharmaceutically acceptable carrier, diluent or excipient.

11. A pharmaceutical composition comprising greater than 80% w/w of a compound which is (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate in crystalline form.

12. A pharmaceutical composition comprising greater than 90% w/w of a compound which is (2R)-1,1,1-trifluoro-3-({cis-4-[(1-methyl-4-{[1-(pyridin-2-yl)-1H-pyrazol-3-yl]amino}-1H-benzimidazol-6-yl)oxy]cyclohexyl}amino)propan-2-ol 2-hydroxypropane-1,2,3-tricarboxylate hydrate in crystalline form.

13. A method of treating a patient in need of treatment for arthritis wherein the method comprises administering to the patient an effective amount of a compound according to claim 1, or a pharmaceutically acceptable salt thereof.

14. The compound according to claim 6 which is:

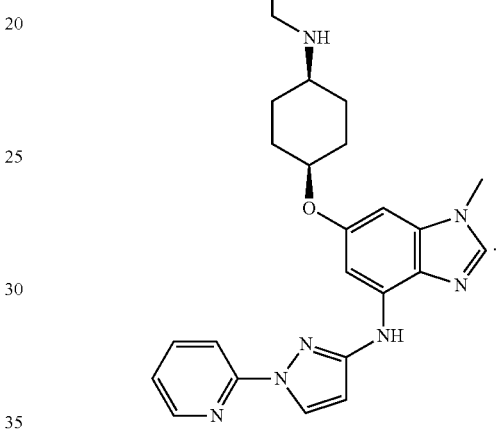

15. A method of treating a patient in need of treatment for ulcerative colitis wherein the method comprises administering to the patient an effective amount of a compound according to claim 6, or a pharmaceutically acceptable salt thereof.

16. A method of treating a patient in need of treatment for Crohn's disease wherein the method comprises administering to the patient an effective amount of a compound according to claim 6, or a pharmaceutically acceptable salt thereof.

17. A method of treating a patient in need of treatment for systemic lupus erythrematosus wherein the method comprises administering to the patient an effective amount of a compound according to claim 6, or a pharmaceutically acceptable salt thereof.

18. A pharmaceutical composition comprising a compound according to claim 6 and a pharmaceutically acceptable carrier, diluent or excipient.

* * * * *